US008152908B2

(12) United States Patent
Masel et al.

(10) Patent No.: US 8,152,908 B2
(45) Date of Patent: Apr. 10, 2012

(54) MICROMACHINED GAS CHROMATOGRAPHY COLUMNS FOR FAST SEPARATION OF ORGANOPHOSPHONATE AND ORGANOSULFUR COMPOUNDS AND METHODS FOR DEACTIVATING SAME

(75) Inventors: Richard I. Masel, Champaign, IL (US); Adarsh D. Radadia, Urbana, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 625 days.

(21) Appl. No.: 12/337,882

(22) Filed: Dec. 18, 2008

(65) Prior Publication Data

US 2009/0211452 A1    Aug. 27, 2009

Related U.S. Application Data

(60) Provisional application No. 61/021,620, filed on Jan. 16, 2008, provisional application No. 61/021,588, filed on Jan. 16, 2008.

(51) Int. Cl.
*B01D 53/02* (2006.01)
(52) U.S. Cl. .......... 96/101; 73/23.39; 95/83; 210/198.2; 427/230
(58) Field of Classification Search .................. 96/101; 95/82, 83; 73/23.39; 210/198.2, 656; 427/230–239
See application file for complete search history.

(56) References Cited

U.S. PATENT DOCUMENTS

| | | | |
|---|---|---|---|
| 2,901,623 A | 8/1959 | Wouters | |
| 3,149,941 A | 9/1964 | Barnitz et al. | |
| 3,168,823 A | 2/1965 | Reinecke et al. | |
| 3,345,858 A | 10/1967 | Fenske | |
| 3,357,232 A | 12/1967 | Lauer | |
| 3,461,519 A | 8/1969 | Raschle | |
| 3,538,744 A | 11/1970 | Karasek | |
| 3,568,411 A | 3/1971 | Dravnicks et al. | |
| 3,585,863 A | 6/1971 | Hrdina | |
| 3,675,466 A | 7/1972 | Linenberg | |
| 3,733,908 A | 5/1973 | Linenberg | |
| 3,769,837 A | 11/1973 | Kraus | |
| 3,797,318 A | 3/1974 | Palm | |
| 3,807,217 A | 4/1974 | Wilkins et al. | |
| 3,897,679 A | 8/1975 | Guild | |
| 3,923,461 A | 12/1975 | Barden | |
| 3,925,022 A | 12/1975 | Showalter et al. | |
| 3,950,980 A | 4/1976 | Braun et al. | |
| 3,985,017 A | 10/1976 | Goldsmith | |
| 4,040,085 A | 8/1977 | Jouanny | |
| 4,040,805 A | 8/1977 | Nelms et al. | |
| 4,084,440 A | 4/1978 | Carpenter et al. | |
| 4,128,008 A | 12/1978 | Linenberg | |
| 4,129,424 A | 12/1978 | Armond | |
| 4,180,389 A | 12/1979 | Paul | |
| 4,235,097 A | 11/1980 | Kring et al. | |
| 4,293,316 A | 10/1981 | Block | |
| 4,293,415 A * | 10/1981 | Bente et al. ................. 210/198.2 |
| 4,301,114 A | 11/1981 | Rounbehler et al. | |
| 4,376,641 A * | 3/1983 | Nestrick et al. .................... 95/83 |
| 4,399,688 A | 8/1983 | Dennis | |
| 4,451,816 A | 5/1984 | Ball | |
| 4,498,850 A | 2/1985 | Perlov et al. | |
| 4,509,964 A * | 4/1985 | Hubball et al. ................. 96/101 |
| 4,541,268 A | 9/1985 | Odernheimer | |
| 4,585,209 A | 4/1986 | Aine et al. | |
| 4,599,095 A | 7/1986 | Barnes et al. | |
| 4,628,576 A | 12/1986 | Giachino et al. | |
| 4,647,013 A | 3/1987 | Giachino et al. | |
| 4,698,071 A | 10/1987 | Elias | |
| 4,701,306 A | 10/1987 | Lawrence et al. | |
| 4,713,091 A | 12/1987 | Govind | |
| 4,735,691 A | 4/1988 | Green et al. | |
| 4,759,210 A | 7/1988 | Wohltjen | |
| 4,778,666 A | 10/1988 | Chu et al. | |
| 4,805,441 A | 2/1989 | Sides et al. | |
| 4,819,477 A | 4/1989 | Fisher et al. | |
| 4,821,999 A | 4/1989 | Ohtaka | |
| 4,826,131 A | 5/1989 | Mikkor | |
| 4,865,746 A * | 9/1989 | Overfield ...................... 210/656 |
| 4,885,830 A | 12/1989 | Ohtaka | |
| 4,895,500 A | 1/1990 | Hok | |
| 4,915,051 A | 4/1990 | Martinek | |
| 4,915,843 A | 4/1990 | Taniguchi et al. | |
| 4,977,095 A | 12/1990 | Zaromb | |
| 4,997,676 A | 3/1991 | Lefebvre | |
| 5,014,541 A | 5/1991 | Sides et al. | |
| 5,055,346 A | 10/1991 | Rohrbacher | |
| 5,069,419 A | 12/1991 | Jerman | |

(Continued)

OTHER PUBLICATIONS

International Search Report, International Preliminary Report on Patentability and the Written Opinion, corresponding to the PCT application PCT/US06/29296 filed Jul. 26, 2006.
International Preliminary Report on Patentability and Written Opinion corresponding to the PCT application PCT/US06/38998 filed Oct. 6, 2006.
International Search Report and Written Opinion corresponding to the PCT application PCT/US07/009243 filed Apr. 13, 2007.
International Preliminary Report and Written Opinion corresponding to the PCT application PCT/US2008/053959 filed Feb. 14, 2008.
Panda, A. B. et al., Microwave Synthesis of Highly Aligned Ultra Narrow Semiconductor Rods and Wires, J. Am. Chem. Soc., 128:2790-2791 (2006).
Tompsett, G. A. et al., Microwave Synthesis of Nanoporous Materials, ChemPhysChem, 7:296-319 (2006).

(Continued)

*Primary Examiner* — Robert Clemente
(74) *Attorney, Agent, or Firm* — Kilpatrick Townsend & Stockton LLP

(57) ABSTRACT

Improved microcolumns and methods for producing microcolumns particularly suitable for use in gas chromatographs are disclosed. In particular, following deposition of the stationary phase coating, the microcolumns are subjected to a postcoating treatment with a molecule that binds to the active sites in the stationary phase column thereby eliminating or reducing loss of gas chromatograph performance associated with those active sites. The postcoating treatment molecule binds to the same active sites as the analytes of interest.

18 Claims, 11 Drawing Sheets

U.S. PATENT DOCUMENTS

| | | |
|---|---|---|
| 5,082,242 A | 1/1992 | Bonne et al. |
| 5,083,019 A | 1/1992 | Spangler |
| 5,092,155 A | 3/1992 | Rounbehler et al. |
| 5,092,217 A | 3/1992 | Achter et al. |
| 5,092,218 A | 3/1992 | Fine et al. |
| 5,110,551 A | 5/1992 | Michal |
| 5,123,276 A | 6/1992 | Hartman et al. |
| 5,142,143 A | 8/1992 | Fite et al. |
| 5,162,652 A | 11/1992 | Cohen et al. |
| 5,173,264 A | 12/1992 | Zaromb et al. |
| 5,176,358 A | 1/1993 | Bonne et al. |
| 5,180,623 A | 1/1993 | Ohnstein |
| 5,216,273 A | 6/1993 | Doering et al. |
| 5,224,972 A | 7/1993 | Frye et al. |
| 5,288,310 A | 2/1994 | Peters et al. |
| 5,294,418 A | 3/1994 | Ramprasad et al. |
| 5,322,258 A | 6/1994 | Bosch et al. |
| 5,323,999 A | 6/1994 | Bonne et al. |
| 5,328,851 A | 7/1994 | Zaromb |
| 5,395,589 A | 3/1995 | Nacson |
| 5,417,235 A | 5/1995 | Wise et al. |
| 5,441,597 A | 8/1995 | Bonne et al. |
| 5,465,607 A | 11/1995 | Corrigan et al. |
| 5,468,851 A | 11/1995 | Seeman et al. |
| 5,481,110 A | 1/1996 | Krishnaswamy et al. |
| 5,482,677 A | 1/1996 | Yao et al. |
| 5,522,918 A | 6/1996 | Shiramizu |
| 5,532,129 A | 7/1996 | Heller |
| 5,551,278 A | 9/1996 | Rounbehler et al. |
| 5,585,575 A | 12/1996 | Corrigan et al. |
| 5,589,396 A | 12/1996 | Frye et al. |
| 5,619,177 A | 4/1997 | Johnson et al. |
| 5,648,508 A | 7/1997 | Yaghi |
| 5,720,798 A | 2/1998 | Nickerson et al. |
| 5,753,832 A | 5/1998 | Bromberg et al. |
| 5,763,360 A | 6/1998 | Gundel et al. |
| 5,795,368 A | 8/1998 | Wright et al. |
| 5,830,427 A | 11/1998 | Bedard et al. |
| 5,836,750 A | 11/1998 | Cabuz |
| 5,854,431 A | 12/1998 | Linker et al. |
| 5,876,830 A | 3/1999 | Michl et al. |
| 5,899,218 A | 5/1999 | Dugan |
| 5,941,501 A | 8/1999 | Biegelsen et al. |
| 5,970,804 A | 10/1999 | Robbat, Jr. |
| 6,000,676 A | 12/1999 | Zengerle et al. |
| 6,026,834 A | 2/2000 | Azima |
| 6,085,601 A | 7/2000 | Linker et al. |
| 6,098,661 A | 8/2000 | Yim et al. |
| 6,110,247 A | 8/2000 | Birmingham et al. |
| 6,126,140 A | 10/2000 | Johnson et al. |
| 6,129,331 A | 10/2000 | Henning et al. |
| 6,165,254 A | 12/2000 | Kawakami et al. |
| 6,171,378 B1 | 1/2001 | Manginell et al. |
| 6,182,941 B1 | 2/2001 | Scheurenbrand et al. |
| 6,187,412 B1 | 2/2001 | Armacost et al. |
| 6,215,221 B1 | 4/2001 | Cabuz et al. |
| 6,223,584 B1 | 5/2001 | Mustacich et al. |
| 6,251,260 B1 | 6/2001 | Heller et al. |
| 6,345,545 B1 | 2/2002 | Linker et al. |
| 6,355,793 B1 | 3/2002 | Lin |
| 6,372,932 B1 | 4/2002 | Kepert et al. |
| 6,384,253 B1 | 5/2002 | Khan |
| 6,454,840 B1 | 9/2002 | Gellert et al. |
| 6,455,003 B1 | 9/2002 | Anvia et al. |
| 6,470,904 B1 | 10/2002 | Tai et al. |
| 6,481,263 B1 | 11/2002 | Haley et al. |
| 6,491,740 B1 | 12/2002 | Wang et al. |
| 6,517,610 B1 | 2/2003 | de la Houssaye |
| 6,523,393 B1 | 2/2003 | Linker et al. |
| 6,527,835 B1 | 3/2003 | Manginell et al. |
| 6,557,820 B2 | 5/2003 | Wetzel et al. |
| 6,568,286 B1 | 5/2003 | Cabuz |
| 6,604,406 B1 | 8/2003 | Linker et al. |
| 6,607,580 B1 | 8/2003 | Hastings et al. |
| 6,607,700 B1 | 8/2003 | Apte et al. |
| 6,610,125 B2 | 8/2003 | Tripp et al. |
| 6,626,416 B2 | 9/2003 | Sharma et al. |
| 6,626,417 B2 | 9/2003 | Winger et al. |
| 6,649,129 B1 | 11/2003 | Neal |
| 6,656,738 B1 | 12/2003 | Vogel et al. |
| 6,663,697 B1 | 12/2003 | Kottenstette et al. |
| 6,666,907 B1 | 12/2003 | Manginell et al. |
| 6,670,024 B1 | 12/2003 | Yu |
| 6,685,841 B2 | 2/2004 | Lopez et al. |
| 6,706,091 B1 | 3/2004 | Robinson et al. |
| 6,719,828 B1 | 4/2004 | Lovell et al. |
| 6,749,826 B2 | 6/2004 | Tillotson et al. |
| 6,759,013 B2 | 7/2004 | Kaltenbach et al. |
| 6,772,513 B1 | 8/2004 | Frye-Mason et al. |
| 6,773,674 B2 | 8/2004 | Bannister et al. |
| 6,783,680 B2 * | 8/2004 | Malik ........................ 210/635 |
| 6,793,753 B2 | 9/2004 | Unger et al. |
| 6,814,781 B2 | 11/2004 | Tonkovich et al. |
| 6,830,229 B2 | 12/2004 | Wetzel et al. |
| 6,834,671 B2 | 12/2004 | Cotte et al. |
| 6,837,476 B2 | 1/2005 | Cabuz et al. |
| 6,838,640 B2 | 1/2005 | Wise et al. |
| 6,840,120 B2 | 1/2005 | Sakairi et al. |
| 6,848,325 B2 | 2/2005 | Parmeter et al. |
| 6,875,257 B2 | 4/2005 | Rodgers |
| 6,893,564 B2 | 5/2005 | Mueller et al. |
| 6,902,701 B1 | 6/2005 | Hughes et al. |
| 6,910,394 B2 | 6/2005 | Kriel |
| 6,913,697 B2 | 7/2005 | Lopez et al. |
| 6,914,220 B2 | 7/2005 | Tian et al. |
| 6,929,679 B2 | 8/2005 | Muller et al. |
| 6,930,193 B2 | 8/2005 | Yaghi et al. |
| RE38,797 E | 9/2005 | Linker et al. |
| 6,965,026 B2 | 11/2005 | Zaworotko et al. |
| 6,967,103 B2 | 11/2005 | Schwartz et al. |
| 6,967,193 B1 | 11/2005 | Dang et al. |
| 6,968,862 B2 | 11/2005 | Cabuz et al. |
| 6,978,657 B1 | 12/2005 | Baumann et al. |
| 6,984,524 B2 | 1/2006 | Nguyen et al. |
| 6,986,365 B2 | 1/2006 | Henning et al. |
| 6,986,500 B2 | 1/2006 | Giousouf et al. |
| 6,989,044 B2 | 1/2006 | Zhang et al. |
| 6,998,040 B2 * | 2/2006 | Malik et al. ............... 210/198.2 |
| 7,000,452 B2 | 2/2006 | Bonne et al. |
| 7,008,193 B2 | 3/2006 | Najafi et al. |
| 7,014,165 B2 | 3/2006 | Ji et al. |
| 7,052,677 B1 | 5/2006 | Raptis et al. |
| 7,147,695 B2 | 12/2006 | Mitra |
| 7,654,129 B2 | 2/2010 | Bonne et al. |
| 7,695,681 B2 | 4/2010 | Wang et al. |
| 2002/0175302 A1 | 11/2002 | Wetzel |
| 2003/0004364 A1 | 1/2003 | Yaghi et al. |
| 2003/0078311 A1 | 4/2003 | Muller et al. |
| 2003/0146401 A1 | 8/2003 | Wetzel |
| 2003/0148165 A1 | 8/2003 | Muller et al. |
| 2003/0222023 A1 | 12/2003 | Mueller et al. |
| 2003/0231967 A1 | 12/2003 | Najafi et al. |
| 2003/0234376 A1 | 12/2003 | Cabuz et al. |
| 2004/0097724 A1 | 5/2004 | Muller et al. |
| 2004/0137300 A1 | 7/2004 | Gemmen et al. |
| 2004/0191125 A1 | 9/2004 | Kellogg et al. |
| 2004/0225134 A1 | 11/2004 | Yaghi et al. |
| 2004/0249189 A1 | 12/2004 | Mueller et al. |
| 2004/0265670 A1 | 12/2004 | Muller et al. |
| 2005/0004404 A1 | 1/2005 | Muller et al. |
| 2005/0067029 A1 | 3/2005 | Henning |
| 2005/0098435 A1 | 5/2005 | Jacobson et al. |
| 2005/0101027 A1 | 5/2005 | Haas |
| 2005/0124819 A1 | 6/2005 | Yaghi et al. |
| 2005/0154222 A1 | 7/2005 | Muller et al. |
| 2005/0164870 A1 | 7/2005 | Shan et al. |
| 2005/0192175 A1 | 9/2005 | Yaghi et al. |
| 2006/0037477 A1 | 2/2006 | Lopez et al. |
| 2006/0049101 A1 | 3/2006 | Suib et al. |
| 2006/0057057 A1 | 3/2006 | Muller et al. |
| 2006/0071192 A1 | 4/2006 | Ohmi et al. |
| 2006/0099398 A1 | 5/2006 | Hesse et al. |
| 2006/0113231 A1 * | 6/2006 | Malik ...................... 210/198.2 |
| 2006/0144237 A1 | 7/2006 | Liang et al. |
| 2006/0175238 A1 * | 8/2006 | Lautamo .................. 210/198.2 |
| 2006/0200044 A1 | 9/2006 | Freeman et al. |
| 2006/0252641 A1 | 11/2006 | Yaghi et al. |

| 2007/0023719 A1 | 2/2007 | Masel et al. |
| 2007/0074717 A1 | 4/2007 | Law et al. |
| 2007/0172960 A1* | 7/2007 | Malik et al. ............ 436/161 |
| 2009/0131643 A1 | 5/2009 | Ni et al. |
| 2009/0178563 A1 | 7/2009 | Masel et al. |
| 2009/0211452 A1 | 8/2009 | Masel et al. |
| 2010/0075123 A1 | 3/2010 | Masel et al. |
| 2010/0132547 A1 | 6/2010 | Masel et al. |

OTHER PUBLICATIONS

Lu, Q. et al., Biomolecule and/or Microwave-Assisted Solvothermal Syntheses of Nanomaterials, AZo Journal of Materials Online vol. 1, (2005).

Grudpan, K. et al., Flow injection spectrophotometric determination of As(III) and As(V) using molybdate reagent with solid phase extraction in-valve column, Indian Journal of Chemistry, 42A:2939-2944 (2003).

Luis Castaner et al., Speed-energy optimization of electrostatic actuators based on Pull-in, IEEE Journal of Microelectromechanical Systems, vol. 8, No. 3, pp. 257-265 (1999).

Han et al., Micro-fabricated membrane gas valves with a non-stiction coating deposited by $C_4F_8$/Ar plasma, J. Micromech. Microeng. 18 (2008) 095015, pp. 1-9.

Yeom et al., The design, fabrication and characterization of a silicon microheater for an integrated MEMS gas preconcentrator, J. Micromech. Microeng. 18 (2008) 125001, pp. 1-12.

Han et al. Surface energy approach and AFM verification of the (CF)n treated surface effect and its correlation with adhesion reduction in microvalves, J. Micromech. Microeng. 19 (2009) 085017, pp. 1-9.

Radadia et al., The fabrication of all-silicon micro gas chromatography columns using gold diffusion eutectic bonding, J. Micromech. Microeng. 20 (2010) 015002, pp. 1-7.

Radadia et al., Micromachined GC Columns for Fast Separation of Organophosphonate and Organosulfur Compounds, Anal. Chem. 2008, 80, pp. 4087-4094.

Radadia et al., Partially Buried Microcolumns for Micro Gas Analyzers, Anal. Chem. 2009, 81, pp. 3471-3477.

Han et al., Smooth Contact Capacitive Pressure Sensors in Touch- and Peeling-Mode Operation, IEEE Sensors Journal, vol. 9, No. 3, Mar. 2009, pp. 199-206.

Radadia et al., The Effect of Microcolumn Geometry on the Performance of Micro-Gas Chromatography Columns for Chip Scale Gas Analyzers, Sensors and Actuators B: Chemical (2010), doi:10.1016/j.snb.2010.07.002, pp. 1-29.

Bae et al., A Bidirectional Electrostatic Microvalve With Microsecond Switching Performance, Journal of Microelectromechanical Systems, vol. 16, No. 6, Dec. 2007, pp. 1461-1471.

Zhong et al., Characterization of a high-performance portable GC with a chemiresistor array detector, Analyst, 2009, 134, pp. 283-293.

Groves et al., Analyzing organic vapors in exhaled breath using a surface acoustic wave sensor array with preconcentration: Selection and characterization of the preconcentrator adsorbent, Analytica Chimica Acta 371 (1998) pp. 131-143.

Zheng Ni, et al., "Rapid Production of Metal-Organic Frameworks via Microwave-Assisted Solvothermal Synthesis," J. Am. Chem. Soc. (2006).

Jay W. Grate, et al., "Progressive Thermal Desorption of Vapor Mixtures from a Preconcentrator with a Porous Metal Foam Internal Architecture and Variable Thermal Ramp Rates," pp. 1867-1875 (2005).

R. W. Jotham, et al., "Anti ferromagnetism in transition-metal complexes. Part IV. Low-lying excited states of binuclear copper (II) carboxylate complexes," J. C. S. Dalton, pp. 428-438 (1971).

K. Tamada, et al., "The steady two-dimensional flow of viscous fluid at low Reynolds numbers passing through an infinite row of equal parallel circular cylinders," Quart. J. Mech. Appl. Math., 10, 1957, 425-432.

H. Hasimoto, "On the periodic fundamental solutions of the Stokes equations and their application to viscous flow past a cubic array of spheres," J. Fluid Mech., 5, 1959, pp. 317-328.

Michinobu Kato, et al., "Copper (II) complexes with subnormal magnetic moments," Richard Chemistry Lab, Tulane University, New Orleans Louisiana, Dec. 20, 1963 pp. 99-128.

Joseph B. Keller, "Viscous flow through a grating or lattice of cylinders," J. Fluid Mech. 18, 1964, 94-96.

Wolfgang Micklitz, et al., Heptadecanuclear mixed metal iron oxo-hydroxo complexes, $[Fe_{16}MO_{10}(OH)_{10}(O_2CPh)_{20}]$ M = Mn or Co, structurally comprised of two fragments derived from $[Fe_{11}O_6(OH)_6(O_2CPh)_{15}]$ Journal American Chemical Society (1989) vol. 111, pp. 6856-6858.

Bernard F. Hoskins, et al "Infinite polymeric frameworks consisting of three dimensionally linked rod-like segments," Journal of the American Chemical Society, vol. 111 No. 15, (1989) pp. 5962-5964.

Sergiu M. Gorun, et al., "Magnetostructural correlations in magnetically coupled (μ-Oxo)diiron(III) complexes," Inorganic Chemistry, 1991, 30(7) pp. 1625-1630.

Vinod S. Nair, et al., "Iron Oxo aggregation: $Fe_3$ to $Fe_6$.Synthesis, structure, and magnetic properties of the hexanuclear dication $[Fe_6(\mu_2 -O)_2 (\mu_2 - OMe)_8(OMe_4(tren)_2]^{2+}$, a soluble, crystalline model of iron Oxo hydroxo nanoparticles, the core of ferritin and rust formation," Inorganic Chemistry (1992) vol. 31, pp. 4048-4050.

Steven C. Shoner, et al., "Neutral catecholate derivatives of manganese and iron: Synthesis and characterization of the metal-oxygen cubane-like species $M_4(DBCat)_2(py)_n$(M =Mn, Fe), the trinuclear complex $Mn_3(DBCat)_4(py)_4$ and the dimers $M_2(DBCat)_2(py)_n$(M =Mn, n =6; M =Fe, n =4,6)," Inorganic Chemistry (1992), 31, pp. 1001-1010.

C.T. Kresge, et al., "Ordered mesoporous molecular sieves synthesized by a liquid-crystal template mechanism," Nature, vol. 359, Oct. 22, 1992, pp. 710-712.

Kingsley L. Taft, et al., "Iron and manganese alkoxide cubes," Journal of American Chemical Society, (1993) vol. 115, pp. 11753-11766.

Andreas Stein, et al., "Turning down the heat: design and mechanism in solid-state synthesis," Science, vol. 259, No. 5101, Mar. 12, 1993, pp. 1558-1564.

Alan Wilson, et al., "Detection of Nitro Compounds by Organic Semiconductor Sensors," Sensors and Actuators B 18-19, 1994, pp. 511-514.

Kingsley L. Taft, et al., "Synthesis, structure, and electronic properties of a mixed-valent dodecairon Oxo complex, a model for the biomineralization of ferritin," Inorganic Chemistry, (1994) 33, pp. 1510-1520.

B.F. Abrahams, et al., "Assembly of porphyrin building blocks into network structures with large channels," Nature vol. 369, Jun. 30, 1994 pp. 727-729.

O.M. Yaghi, et al., "Hydrothermal Synthesis of a Metal-Organic Framework Containing Large Rectangular Channels," J. Am. Chem. Soc. 1995, 117, 10401-10402.

Katerina Dimitrou, et al., "The $[CO_4O_4]^{4+}$ cubane as a quadruply-bridging unit: the mixed-valence cluster $[Co_8O_4(O_2CPh)_{12}solv_4]$ solv = DMF, MeCN, $H_2O$)," Inorganic Chemistry, 1995, 34, pp. 4160-4166.

O. M. Yaghi, et al., "Hydrothermal synthesis of a metal-organic framework containing large rectangular channels," Journal of the American Chemical Society, 1995, vol. 117, pp. 10401-10402.

O.M. Yaghi, et al., "Selective Binding and Removal of Guests in a Microporous Metal-Organic Framework," Nature, Dec. 14, 1995, vol. 378, pp. 703-706.

O.M. Yaghi, et al., "T-Shaped Molecular Building Units in the Porous Structure of Ag(4,4'-bpy)•$NO_3$," J. Am. Chem. Soc. 1996, 118, pp. 295-296.

O. M. Yaghi, et al., "Construction of porous solids from hydrogen-bonded metal complexes of 1,3,5-benzenetricarboxylic acid," Journal of the American Chemical Society, (1996), vol. 118, pp. 9096-9101.

William A. Groves, et al., "Prototype Instrument Employing a Microsensor Array for the Analysis of Organic Vapors in Exhaled Breath," American Industrial Hygiene Association Journal 57:1103-1108, Dec. 1996.

Scott Hynek, et al., "Hydrogen storage by carbon sorption," Int. J. Hydrogen Energy vol. 22, No. 6, pp. 601-610 (1997).

Jian Lu, et al., "Coordination Polymers of $Co(NCS)_2$ with Pyrazine and 4,4'-Bipyridine: Syntheses and Stuctures," Inorganic Chemist (1997) vol. 36, pp. 923-929.

Christoph Janiak, "Functional organic analogues of zeolites bases on metal-organic coordination frameworks," Angew. Chem. Int. Ed. Engl. (1997) 36, No. 13/14 pp. 1431-1434.

Mario V. Capparelli, et al., "X-ray crystallographic structure of $Ga_8(pz)_{12}O_4Cl_4 \cdot 2thf$: a novel gallium pyrazololate complex with a $Ga_4O_4$ core," Chem. Comm., (1997) pp. 937-938.

O. M. Yaghi, et al., "Crystal growth of extended solids by nonaqueous gel diffusion," Chemical Materials, (1997) vol. 9, pp. 1074-1076.

Omar M. Yaghi, et al., "Construction of a new open-framework solid from 1,3,5-cyclohexane-tricarboxylate and zinc(II) building blocks," Journal Chem. Soc. Dalton Trans., (1997), pp. 2383-2384.

Victoria A. Russell, et al,, "Nanoporous molecular sandwiches: pillared two-dimensional hydrogen-bonded networks with adjustable porosity," Science, vol. 276, Apr. 25, 1997, pp. 575-579.

Helmut Beinert, et al., "Iron-sulfur clusters: Nature's modular, multipurpose structures," Science, vol. 277, Aug. 1997, pp. 653-659.

Omar M. Yaghi, et al., "Synthetic Strategies, Structure Patterns, and Emerging properties in the chemistry of modular porous solids," Accounts of Chemical Research, vol. 31, No. 8, 1998, pp. 474-484.

William A. Groves, et al., "Analyzing organic vapors in exhaled breath using a surface acoustic wave sensor array with preconcentration: Selection and characterization of the preconcentrator adsorbent," Analytica Chimica Acta 371, 1998, pp. 131-143.

Michael W. Willer, et al., "Ligand Substitution Reactions of $[Re_6S_8Br_6]^{4-}$: A Basis Set of $Re_6S_8$ Clusters for Building Multicluster Assemblies," Inorganic Chemistry, (1998) vol. 37, pp. 328-333.

Hailian Li, et al., "Coordinatively unsaturated metal centers in the extended porous framework of $Zn_3(BDC)_3 \cdot 6CH_3OH$ (BDC =1,4-benzenedicarboxylate)," Journal of American Chemical Society, 1998, vol. 120, pp. 2186-2187.

Stuart L. James, et al., "Anion-templated formation of a unique inorganic 'super adamantoid' cage $[Ag_6(triphos)_4(O_3SCF_3)_4]^{2+}[triphos = (PPh_2CH_2)_3CMe]$," Chemical Communication (1998) pp. 2323-2324.

M. John Plater, et al., "Hydrothermal synthesis and characterization of $M(pdc) \cdot 3H_2O$ (pdc =2,5-pyridinedicarboxylate); M=Co, Ni, $Co_xNi_y(x=0.4-0.6, y=0.6-0.4)$," Journal of Chemical Research, (1998), pp. 3356-3376.

Cameron J. Kepert, et al., "A porous chiral framework of coordinated 1,3,5- benzenetricarboxylate: quadruple interpenetration of the (10,3)-a network," Chem Communication (1998) pp. 31-32.

Christopher W. Jones, et al., "Organic-functionalized molecular sieves as shape-selective catalysts," Nature vol. 393, May 7, 1998, . 52-54.

Lin, et al., "A Novel Ocupolar Metal-Organic NLO Material Based on a Chiral 2D Coordination Network," J. Am Chem. Soc. 1999, 121, 11249-11250.

Chui, et al., "A Chemically Functionalizable Nanoporous Material $[Cu_3(TMA)_2(H_2O)_3]n$," Science, 1999, vol. 283, pp. 1148-1150.

Jack Y. Lu, et al., "A new type of Two-Dimensional Metal Coordination Systems: Hydrothermal Synthesis and Properties of the First Oxalate-bpy Mixed-Ligand Framework $2[(M (ox)(bpy)]$ (M=Fe(II), CO(II), Ni(II), Zn(II); $ox = C_2O_4^{2-}$; bpy =4,4'-bipyridine)," Inorganic Chem. 1999, 38, pp. 2695-2704.

Srinivasan Natarajan, et al., "Layered Tin (II) Oxalates possessing large apertures," Chemical Material, 1999, 11 pp. 1633-1639.

Mitsuru Kondo, et al., "Rational synthesis of stable channel—like cavities with methane gas adsorption properties: $[\{Cu_2(pzdc)_2(L)\}_n]$ (pzdc =pyrazine-2,3-dicarboxylate; L=a pillar ligand)," Angew. Chem. Int. Ed. (1999) 38, No. ½, pp. 140-143.

Raphael G. Paptis, et al., "A $Fe^{III}$/Oxo cubane contained in an octanuclear complex of T symmetry that is stable over., five oxidation states," Angew, Chem. Int. Ed. (1999), vol. 38, No. 11, pp. 1632-1634.

Mohamed Eddaoudi, et al., "Design and synthesis of metal-carboxylate frameworks with permanent microporosity," Topics in Catalysis, 1999, vol. 9, pp. 105-111.

Stephen S.-Y Chui, et al., "A chemically functionalizable nanoporous material $[Cu_3(TMA)_2(H_2O)_3]_n$," Science, vol. 283, Feb. 19, 1999, pp. 1148-1150.

Hailian Li, et al., "Design and synthesis of an exceptionally stable and highly porous metal-organic framework," Nature, vol. 402, Nov, 18, 1999, pp. 276-279.

Seo, et al., "A Homochiral Metal-organic Porous Material for Enantioselective Separation and Catalysis," Nature, 2000, 404, pp. 982-986.

Jeongim Park, et al., "Temperature and Humidity Compensation in the Determination of Solvent Vapors with a Microsensor System," The Royal Society of Chemistry, Analyst, 2000, 125, pp. 1775-1782.

Edward T. Zellers, et al., "Evaluating Porous-Layer Open-Tubular Capillaries as Vapor Preconcentrators in a Microanalytical System," Sensors and Actuators B 67, 2000, pp. 244-253.

Qing-Yun Cai, et al., "Vapor Recognition with an Integrated Array of Polymer-Coated Flexural Plate Wave Sensors," Sensors and Actuators B 62, 2000, pp. 121-130.

M.O. O'Keeffe, et al., "Frameworks for extended solids: geometrical design principles," Journal of Solid State Chemistry 152, pp. 3-20, 2000.

Shouheng Sun, et al., "Monodisperse FePt nanoparticles and ferromagnetic FePt nanocrystals superlattices," Science. vol. 287, Mar. 17, 2000, pp. 1989-1992.

Xi Xiang Zhang, et al., "Cooperative magnetic behavior in the coordination polymers $[Cu_3(TMA)_2L_3]$ ($L=H_2O$, pyridine)," Journal of Applied Physics, vol. 87, No. 9 May 1, 2000, pp. 6007-6009.

R. Murugavel, et al., "Extended metal-organic solids based on benzenepolycarboxylic and aminobenzoic acids," Proc. Indian Acad. Sci. (Chem. Sci.) vol. 112, No. 3, Jun. 2000, pp. 273-290.

Jaheon Kim, et al., "Assembly of Metal-Organic Frameworks from Large Organic and Inorganic Secondary Building Units: New Examples and Simplifying Principles for Complex Structures," J. Am. Chem. Soc. 2001, 123, pp. 8239-8247.

Banglin Chen, et al., "Interwoven Metal-Organic Framework on a Periodic Minimal Surface with Extra-Large Pores," Science, Feb. 9, 2001, vol. 291, pp. 1021-1023.

Usan A. Bourne, et al., "Coexisting Covalent and Noncovalent Nets: Parallel Interpenetration of a Puckered Rectangular Coordination Polymer and Aromatic Noncovalent Nets," Chcm. Comm., 2001, pp. 861-862.

Chang-Ge Zheng, et al., "A novel two-dimensional layer network composed of cadmium and bridging isophthalate ligand," Inorganic Chemistry Communications 4, (2001), pp. 165-167.

Brian Moulton, et al., "From molecules to crystal engineering: supramolecular isomerism and polymorphism in network solids," Chemical Reviews, 2001, vol. 101 No. 6, pp. 1629-1658.

Cynthia Stowell, et al., "Self-Assembled honeycomb networks of gold nanocrystals," Nanoletters, (2001) vol. 1, No. 11, pp. 595-600.

Yucang Liang, et al., "Hydrothermal synthesis and characterization of the coordination polymer $[Zn(bbdc)(H_2O)]_n$(bbdc =4,4'-bibenzene-dicarboxylate) possessing a 3D network structure," Inorganic Chemistry Communications 4 (2001) pp. 599-601.

Yen-Hsiang Liu, et al., "Hydrothermal synthesis, crystal structure, and magnetic property of copper (II) coordination networks with chessboard tunnels," Journal of Solid State Chemist 158 2001 vol. 158, pp. 315-319.

Chuan-De Wu, et al., "Hydrothermal synthesis of two new zinc coordination polymers with mixed ligands," Inorganic Chemistry Communications 4 (2001) pp. 561-564.

H. Tamura, et al., "Semiconductor ferromagnetism in quantum dot array," Physical Stat. Sol. (b) 224, No. 3, (2001), pp. 723-725.

Ashleigh J. Fletcher, et al., "Adsorption dynamics of gases and vapors on the nanoporous metal organic framework material $Ni_2(4,4'$-$bipyridine)_3(NO_3)_4$: Guest modification of host sorption behavior," Journal of the American Chemical Society (2001), vol. 123, pp. 10001-10011.

Kumar Biradha, et al., "2D and 1D coordination polymers with the ability for inclusion of guest molecules: nitrobenzene, benzene, alkoxysilanes," Journal of Inclusion Phenomena and Macrocyclic Chemistry 49, (2001) pp. 201-208.

Mohamed Eddaoudi, et al., "Modular Chemistry: Secondary building units as a basis for the design of highly porous and robust metal-organic carboxylate frameworks," Acc. Chem. Res. 2001, vol. 34, pp. 319-330.

Jaheon Kim, et al., "Assembly of metal-organic frameworks from large organic and inorganic secondary building units:. new examples and simplifying principles for complex stntctures," Journal of the American Chemical Society, (2001), vol. 123, pp. 8239-8247.

Susan A. Bourne, et al., "Self-assembly of nanometer-scale secondary building units into an undulating two-dimensional network with two types of hydrophobic cavity," Angew. Chem. Int. Ed., (2001), vol. 40, No. 11, pp. 2111-2113.

Jianjiang Lu, et al., "Polygons and faceted polyhedra and nanoporous networks," Angew. Chem. Int. Ed., (2001), vol. 40, No. 11, pp. 2113-2116.

Brian Moulton, et al., "Nanoballs: nanoscale faceted polyhedra with large windows and cavities," Chem. Commun., (2001), pp. 863-864.

Heba Abourahma, et al., "Hydroxylated nanoballs: synthesis, crystal structure, solubility and crystallization on surfaces," Chem. Comm., (2001), pp. 2380-2381.

Susan A. Bourne, et al., "1-D coordination polymers containing benzenedicarboxylate," Crystal Engineering, (2001), vol. 4, pp. 25-36.

Chia-Jung Lu, et al., "A Dual-Adsorbent Preconcentrator for a Portable Indoor-VOC Microsensor System," Analytical Chemistry, vol, 73, No. 14, Jul. 15, 2001, pp. 3349-3457.

Kosal, M.E., et al., "A functional zeolite analogue assembled from metalloporphyrins," Nature Materials, 2002, vol. 1, pp. 118-121.

Xingling Xu, et al., "A nanoporous metal-organic framework based on bulky phosphane ligands," Angew. Chem. Int. Ed, (2002) 41, No. 5 pp. 764-767.

Filipe A. Almeida Paz, et al., "Synthesis and characterization of a novel modular cadmium-organic framework with biphenyl-4,4'-dicarboxylate," Eur. J. Inorg, Chem. (2002) pp. 2823-2828.

Zi-Guang Sun, et al., "Guest controlled coordination framework: syntheses, crystal structures and thermal properties of two three-dimensional structures of $[Ce_2(adipate)_3(OH_2)_4]$• $6H_2O$ and $[Ce_2(adipate)_3(OH_2)_4]$• $4H_2O$ • (adipic acid)," Inorganic Chemist Communications 5 (2002) pp. 629-632.

Ljiubov Morris, et al., "Simple system for part-per-billion-level volatile organic compound analysis in groundwater and urban air," Measurement Science and Technology, 13, (2002) pp. 603-612.

Ming Wen, et al., "Porous silver (I) organometallic coordination polymer of triptycene, and the guest desorption and absorption," Inorganica Chimica Acta 340 (2002) pp. 8-14.

Edmund J. Cussen, et al., "Flexible sorption and transformation behavior in a microporous metal-organic framework," Journal of the American Chemical Society (2002), vol. 124, pp. 9574-9581.

Yu-Cang Liang, et al., "Hydrothermal syntheses, structural characterizations and magnetic properties of cobalt (II) and manganese(II) coordination polymeric complexes containing pyrazinecarboxylate ligand," Inorganica Chimica Acta 328, (2002), pp. 152-158.

Jun Tao, et al., "Assembly of a microporous metal-organic framework [Zn(bpdc)(DMSO)] (bpdc = 4,4-biphenyldicarboxylate) based on paddle-wheel units affording guest inclusion," Inorganic Chemistry Communications, (2002), vol. 5, pp. 975-977.

Mohamed Eddaoudi, et al., "Systematic Design of Pore Size and Functionality in Isoreticular MOFs and Their Application in Methane Storage," Science, Jan. 18, 2002, vol. 295, pp. 469-472.

Yaghi, et al., "Reticular Synthesis and the Design of New Materials," Nature 423, 2003, pp. 705-714.

Smithenry, D.W., et al., "A Robust Microporous Zinc Porphyrin Framework Solid," Inorg. Chem. 2003, vol. 42, pp. 7719-7721.

Jinxi Chen, et al., "A new open metal-organic framework $[(Zn_8(GeO_4)(C_8H_4O_4)_6)_n$, Constucted by Heterometallic Cluster $Zn_8(GeO_4)$ Secondary Building Units," Chemist Letters vol. 32, No. 5 (2003).

Enrique Colacio, et al., "Hydrothermal syntheses, crystal structures, and properties of two- dimensional homo- and heterometallic cyanide-bridged complexes: $[CU_2(CN)_2(bpym)]$ and $[Fe((bipy)_2(CN)_4CU_2]$ [(bpym =2,2'—Bipyrimidine, bipy =2,2'-Bipyridine)," Inorganic Chemist 2003, 42, pp. 4209-4214.

Li-Ping Zhang, et al., "Hydrothermal synthesis and crystal structures of three novel lanthanide coordination polymers with glutarate and 1,10 phenanthroline," Journal of Molecular Structure 646 (2003) pp. 169-178.

Li-Ping Zhang, et al., "Hydrothermal synthesis and crystal structure of neodymium(III) coordination polymers with isophthalic acid and 1,10-phenanthroline," Polyhedron 22 (2003) pp. 981-987.

Hidekazu Arii, et al., "Unique three-dimensionally expanded nanoporous structure constructed with a Cu(I) and cis, cis-1,3 ,5-triaminocyclohexane having a 3-fold axial symmetry," Chemist Letters vol. 32 No. 1 (2003) pp. 106-107.

Aleksey Vishnyakov, et al., "Nanopore structure and sorption properties of Cu-BTC metal-organic framework," Nano Letters, vol. 3, No. 6, (2003) pp. 713-718.

T. J. Prior, et al., "Designed layer assembly: a three-dimensional framework with 74% extra-framework volume by connection of infinite two-dimensional sheets," Chem. Commun., (2003), pp. 500-501.

Yang-Guang Li, et al., A novel three-dimensional metal-organic framework constructed from two-dimensional interpenetrating layers based on trinuclear cobalt clusters: $[Co_3(btec)(C_2O_4)(H_2O_2]_n$, Eur. Journal of Inorganic Chemistry (2003) pp. 2567-2571.

Sujit K. Ghosh, et al., "Coexistence of water dimer and hexamer clusters in 3D metal-organic framework structures of Ce(III) and Pr(III) with pyridine-2 6-dicarboxylic acid," Inorganic Chemistry, (2003) vol. 42, pp. 8250-8254.

Hee K. Chae, et al., "Design of frameworks with mixed triangular and octahedral building blocks exemplified by the structure of $[Zn_4O(TCA)_2]$ having the pyrite topology," Angew. Chem. Int. Ed., (2003), vol. 42, pp. 3907-3909.

Nathaniel L. Rosi, et al., "Hydrogen Storage in Microporous Metal-Organic Frameworks," Science, May 16, 2003, vol. 300, pp. 1127-1129.

Wei-Cheng Tian, et al., "Microfabricated Preconcentrator-Focuser for a Microscale Gas Chromatograph," Journal of Microelectromechanical Systems, vol. 12, No. 3, Jun. 2003, pp. 264-272.

Yun-Qi Tian, et al., "$\{[In_3(pzdc)_6]^{3-}\{$ Metal-Organic Framework of Distorted NbO-like Net (pzdc =Pyrazine-2,3-dicarboxylato)," Chemistry Letters vol. 32, No. 9, pp. 796-797, Aug. 4, 2003.

Jason K. Holt, et al., "Fabrication of a Carbon Nanotube-Embedded Silicon Nitride Membrane for Studies of Nanometer-Scale Mass Transport," American Chemical Society, Nano Letters 2004, vol. 4, No. 11, pp. 2245-2250.

Jessee L.C. Rowsell, et al., "Metal-organic frameworks: a new class of porous materials," Microporous and Mesoporous Materials 73, 2004, pp. 3-14.

Suman Mukhopadhyay, et al., "Honeycomb Nets with Interpenetrating Frameworks Involving Iminodiacetato-Copper (II) Blocks and Bipyridine Spacers: Syntheses, Characterization, and Magnetic Studies," Inorganic Chemistry, 2004, 43, pp. 3413-3420.

Mind-Hua Zeng, et al., "Crystal-to-crystal transformations of a microporous metal-organic laminated framework triggered by guest exchange, dehydration and readsorption," Dalton Trans., 2004, pp. 2217-2223.

Junji Ito, et al., "Discrimination of halitosis substance using QCM sensor array and a preconcentrator," Sensors and Actuators B 99 (2004) pp. 431-436.

Qiang Wei, et al., "A manganese metal-organic framework which remains crystalline on desolvation, and which gives insight into the rotational freedom of framework aromatic groups," Microporous and Mesoporous Materials 73 (2004) pp. 97-100.

Xiang-Jun Zheng, et al., "Hydrothermal syntheses, structures and magnetic properties of two transition metal coordination polymers with a square grid framework," Polyhedron 23, (2004) pp. 1257-1262.

Klaus Schlichte, et al., "Improved synthesis, thermal stability and catalytic properties of the metal-organic framework compound $Cu_3(BTC)_2$," Microporous and Mesoporous Materials 73 (2004) pp. 81-88.

Danil N. Dybtsev, et al., "Rigid and flexible: A Highly Porous Metal-Organic Framework with Unusual Guest-Dependent Dynamic Behavior," Angew. Chem. Int. Ed. (2004) 43, pp. 5033-5036.

Danil N. Dybtsev, et al., "Three-dimensional metal-organic framework with (3,4)-connected net, synthesized from an ionic liquid medium," Chem. Commun. (2004) pp. 1594-1595.

Ryo Kitaura, et al., "Rational Design and Crystal Structure Determination of a 3-D Metal-Organic Jungle-Gym-Like Open Framework," Inorganic Chemist (2004), vol. 43, No. 21, pp. 6522-6524.

Filipe A. Almeida Paz, et al., "Synthesis and Characterization of a Novel Cadmium-Organic Framework with Trimesic Acid and 1,2-Bis(pyridl)ethane," Inorganic Chemistry (2004),vol. 43, No. 13, pp. 3948-3954.

Eithne Tynan, et al., "Solvent templated synthesis of metal-organic frameworks: structural characterization and properties of the 3D network isomers ([Mn(dcbp)] • ½DMF}$_n$ and {[Mn(dcbp)] • 2H$_2$O)$_n$," Chem. Comm. (2004), pp. 776-777.

Haitao Xu, et al., "Two new microporous coordination polymers constructed by ladder-like and ribbon-like molecules with cavities," Journal of Molecular Structure 693 (2004) pp. 11-15.

Cheng-Yong Su, et al., "A three-dimensional, noninterpenetrating metal-organic framework with the moganite topology: a simple ($4^2$.$6^2$.$8^2$)($4.6^4$.$8$)$_2$net containing two kinds of topologically nonequivalent points," Inorganic Chemistry Communication (2004), vol. 43, pp. 6881-6883.

Cheng-Yong Su, et al., "Exceptionally stable, hollow tubular metal-organic architectures: synthesis, characterization, and solid-state transformation study," Journal of the American Chemical Society, (2004) vol. 126, pp. 3576-3586.

Giannis S. Papaefstathiou, et al., "A 2D metal-organic framework with two different rhombus-shaped cavities: a rare example of a (4,4)-net with alternating metal and organic nodes," Microporous and Mesoporous Materials 71(2004) pp. 11-15.

Yan Bai, et al., "A three dimensional porous metal-organic framework [Fe$_6$$_4$L$_6$•(DMF)$_3$• (H$_2$O)$_{10}$] constructed from neutral discrete Fe$_4$L$_6$ pyramids [H$_2$L = 1,3-benzodihydroxamic acid]," Chem, Commun., (2004) pp. 186-187.

M. J. Rosseinsky, "Recent developments in metal-organic framework chemistry: design, discovery, permanent porosity and flexibility," Microporous and Mesoporous Materials 73(2004), pp. 15-30.

Hye Jin Choi, et al., "Dynamic and redox active pillared bilayer open framework: single-crystal-to-single crystal transformations upon guest removal, guest exchange, and framework oxidation," Journal of the American Chemical Society, (2004), vol. 126, pp. 15844-15851.

Ashleigh J. Fletcher, et al., "Adsorption of gases and vapors on nanoporous Ni$_2$(4,4'-bipyridine)$_3$(NO$_3$)$_4$ metal-organic framework materials templated with methanol and ethanol: structural effects in adsorption kinetics," Journal of the American Chemical Society, (2004), vol. 126, pp. 9750-9759.

Xinlong Wang, et al., "Designed double layer assembly: a three-dimensional open framework with two types of cavities by connection of infinite two-dimensional bilayer," Chem. Comm., (2004), pp. 378-379.

Yaqin Guo, et al., "Synthesis and Crystal Structure of a Novel Three-Dimensional Supramolecular Network Containing One-Dimensional Honeycomb-Like Channels," Inorganica Chimica Act vol. 357, (2004) pp. 4582-4586.

Liying Duan, et al., "Hydrothermal synthesis and crystal structures of two novel rare earth coordination polymers based on pyridine-2,6-dicarboxylic acid," Journal of Molecular Structure 689, (2004) pp. 269-274.

Sujit K. Ghosh, et al., "Puckered-boat conformation hexameric water clusters stabilized in a 2D metal-organic framework structure built from Cu(II) and 1,2,4,5-benzenetetracarboxylic acid," Inorganic Chemistry, (2004), vol. 43, pp. 5180-5182.

Hee K. Chae, et al., "A route to high surface area, porosity and inclusion of large molecules in crystals," Nature, vol. 427, Feb. 2004, pp. 523-527.

Xuebo Zhao, et al., "Hysteretic adsorption and desorption of hydrogen by nanoporous metal-organic frameworks," Science, vol. 306, Nov. 5, 2004, pp. 1012-1015.

Dat T. Tran, et al., "Open Metal-Organic Framework Containing Cuprate Chains," Inorganic Chemistry, vol. 44, No. 18, 2005, pp. 6192-6196.

Chia-Jung Lu, et al., "First-Generation Hybrid MEMS Gas Chromatograph," Lab on a Chip, 2005, 5, pp. 1123-1131.

C.E. Davis, et al., "Enhanced Detection of *m*-xylene Using a Preconcentrator with a Chemiresistor Sensor," Sensors and Actuators B 104, 2005, pp. 207-216.

A.T. Carvalho, et al., "Improvement on Organic Compound Adsorption and/or Detection by Using Metallic Thin Films Deposited onto Highly Rough Silicon Substrates," Sensors and Actuators B 108, 2005, pp. 947-954.

Yanjun Tang, et al., "A Micro-post Preconcentrator for a Microscale Gas Chromatography System," 2005 Micro Total Analysis Systems Conference (Boston, MA, Oct. 2005); Transducers Research Foundation Proceedings of the 2005 Micro Total Analysis Systems Conference, p. 660-662 (2005).

Bing-Bing Ding, et al., "Pillared-Layer Microporous Metal-Organic Frameworks Constructed by Robust Hydrogen Bonds. Synthesis, Characterization, and Magnetic and Adsorption Properties of 2,2'-Biimidazole and Carboxylate Complexes," Inorganic Chemist vol. 44, No. 224, 2005, pp. 8836-8845.

Qianrong Fang, et al., "A metal-organic framework with the ziolite MTN Topology containing large cages of vol. 2.5 nm$^3$," Angew. Chem. Int. Ed. 2005, 44, pp. 3845-3848.

Banglin Chen, et al., "High H$_2$ adsorption in a microporous metal-organic framework with open metal sites," Angew. Chem. Int. Ed. 2005, 44, pp. 4745-4749.

Drew L, Murphy, et al., "A chiral, heterometallic metal-organic framework derived from a tris(chelate) coordination complex," Chemist Communication, 2005, pp. 5506-5508.

Radu Custelcea, et al., "A metal-organic framework functionalized with free carboxylic acid sites and its selective binding of a Cl(H$_2$O)$_4$—cluster," J. Am. Chem. Soc. 2005, 127, pp. 16362-16363.

Thomas Devic, et al., "MIL-103, A 3-D lanthanide-based metal organic framework with large one-dimensional tunnels and a high surface area," J. Am. Chem. Soc. 2005, 127, pp. 12788-12789.

Jarrod F. Eubank, et al "Terminal co-ligand directed synthesis of a neutral, non-interpenetrated (10,3)-α metal-organic framework," Chemical Communication, 2005, pp. 2095-2097.

Lei Wang, et al., "Two-dimensional metal-organic framework constructed from 4,4'-bipydine and 1,2,4-benzenetricarboxylate: synthesis, structure and magnetic properties," Journal of Solid State Chemistry, 178 (2005) pp. 3359-3365.

Ru-Qiang Zou, et al., "A hydrogen-bonded 3D coordination network of Co$^{II}$ with 4-(*p*-benzoxy)-1,2,4-triazole: hydrothermal synthesis, characterization, crystal structure and emission property," Journal of Molecular Structure 737 (2005) pp. 125-129.

Jun Hong, "[Zn$_2$(BTDA)(bpy)(H$_2$O)]•0.5bpy: a new three-dimensional metal-organic framework constructed from flexible and rigid mixed ligands," Journal of Molecular Structure 752 (2005) pp. 166-169.

Henrik Fano Clausen, et al., "Solvothermal synthesis of new metal organic framework structures in the zinc-terephthalic acid-dimethyl formamide system" Journal of Solid State Chemist 178, (2005) pp. 3342-3351.

Giovanni Garberoglio, et al., "Adsorption of gases in metal organic materials: comparison of simulations and experiments," Journal of Physical Chemist B (2005) 109, pp. 13094-13103.

Gregory J. Halder, et al., "in situ single-crystal x-ray diffraction studies of desorption and sorption in a flexible nano porous molecular framework material," Journal of the American Chemical Society (2005), 127, pp. 7891-7900.

Ryo Kitaura, et al., "Formation and characterization of crystalline molecular arrays of gas molecules in a 1-dimensional ultramicropore of a porous copper coordination polymer," Journal of Physical Chemist B, (2005) 109, pp. 23378-23385.

Zheming Wang, et al., "Synthesis and characterization of a porous magnetic diamond framework, Co$_3$(CHOO)$_6$, and its N$_2$ sorption characteristic," Inorganic Chemist (2005), vol. 44, No. 5, pp. 1230-1237.

Hendrik Dathe, et al., "Metal organic frameworks based on Cu$^{2+}$ and benzene-1,3,5-tricarboxylate as host for SO$_2$ trapping agents," C. R. Chimie 8 (2005) pp. 753-763.

Jeong Yong Lee, et al., "Gas sorption properties of microporous metal organic frameworks," Journal of Solid State Chemist 178 (2005) pp. 2527-2532.

Jeong Yong Lee, et al., "Achieving high density of adsorbed hydrogen in microporous metal organic frameworks," Advanced Materials (2005) vol. 17, pp. 2703-2706.

Carine Livage, et al., "A three-dimensional metal-organic framework with an unprecedented octahedral building unit," Angew. Chem. Int. Ed. (2005) vol. 44, pp. 6488-6491.

Andrea M. Goforth, et al., "Connecting small ligands to generate large tubular metal-organic architectures," Journal of Solid State Chemist 178, (205) pp. 2511-2518.

Linhua Xie, et al., "A three-dimensional porous metal-organic framework with the rutile topology contructed from triangular and distorted octahedral building blocks," Chem. Comm., (2005) pp. 2402-2404.

Giannis S. Papaefstathiou, et al "Design and construction of a 2D metal organic framework with multiple cavities: a nonregular net with a paracyclophane that codes for multiply fused nodes," Journal of the American Chemical Society, vol. 127, No. 41 (2005) pp. 14160-14161.

O. I. Lebedev, et al., "First direct imaging of giant pores of the metal-organic framework MIL-101," Chemistry Materials, (2005), vol. 17, pp. 6525-6527.

Dat T. Tran, et al., "Open metal-organic framework containing cuprate chains," Inorganic Chemistry, (2005) vol. 44, No. 18, pp .6192-6196.

Ashleigh J. Fletcher, et al., "Flexibility in metal-organic framework materials: Impact on sorption properties," Journal of Solid State Chemist 178, (2005) pp. 2491-2510.

Tatsuhiko Sagara, et al., "New isoreticular metal-organic framework materials for high hydrogen storage capacityj," The Journal of Chemical Physics 123, 214707 (2005), pp. 1-6.

Tatsuhiko Sagara, et al., "Binding energies of hydrogen molecules to isoreticular metal-organic framework materials," The Journal of Chemical Physics 123, 014701 (2005), pp. 1-4.

Eun Young Lee, et al,, "Multifunctionality and crystal dynamics of a highly stable, porous metal-organic framework $[Zn_4O(NTB)_2]$" Journal of the American Chemical Society (2005) vol. 127, pp. 6374-6381.

Xiao-Jun Zhao et al., "A three-dimensional zinc trimesate framework: $[(CH_3)_2NH_2]$ $[Zn(C_9H_3O_6)]$ • $(C_3H_7NO)$," Applied Organometallic Chemistry (2005), vol. 19, pp. 694-695.

D. Maspoch, et al., "EPR characterization of a nanoporous metal-organic framework exhibiting a bulk magnetic ordering," Journal of Physics and Chemistry of Solids, (2005), vol. 65, pp. 819-824.

Xin-Long Wang, et al., "An unprecedented eight-connected self-penetrating network based on pentanuclear zinc cluster building blocks," Chem. Communication, (2005), pp. 4789-4791.

Xiuli Bai Yangguang Li, et al., "A novel three- dimensional hybrid framework based on fishbone-like copper halide inorganic units," Inorganica Chimica Acta 358, (2005), pp. 2571-2574.

Jorge Gonzalez, et al., "Deuterium NMR studies of framework and guest mobility in the metal-organic framework compound MOF-5, $Zn_4O(O_2CC_6H_4CO_2)_3$," Microporous and Mesoporous Materials 84, (2005), pp. 97-104.

Ru-Qiang Zou, et al., "Rational assembly of a 3D metal-organic framework for gas adsorption with predesigned cubic building blocks and 1D open channels," Chem, Commun., (2005) pp. 3526-3528.

Yi-Hang Wen, et al., Hydrothermal syntheses, crystal structures and characterizations of three new copper coordination polymers, Inorganica Chimica Acta 358 (2005) pp. 3347-3354.

Sujit K. Ghosh, et al., "Infinite chains of quasi-planar hexameric water clusters stabilized in a metal-organic framework built from $Co^{II}$ and pyrazine-2,3,5,6-tetracarboxylic acid," Eur. Journal of Inorganic Chemistry (2005), pp. 4880-4885.

Miguel Fuentes-Cabrera, et al., "Electronic structure and properties of isorcticular metal-organic frameworks: the case of M-IRMOF1 (M=Zn, Cd, Be, Mg, and Ca)," The Journal of Chemical Physics vol. 123, (2005), 124713, pp. 1-5.

Jianghua He, et al., "Synthesis, structure, and luminescent property of a heterometallic metal-organic framework constructed from rod-shaped secondary building blocks," Inorganic Chemistry, (2005) vol. 44, pp. 9279-9282.

Andrew R. Millward, et al., "Metal-organic frameworks with exceptionally high capacity for storage of carbon dioxide at room temperature," Journal of the American Chemical Society (2005), vol. 127, pp. 17998-17999.

Banglin Chen, et al., "Transformation of a metal-organic framework from the NbO to PtS net," Inorganic Chemistry, (2005), vol. 44, pp. 181-183.

Zhenqiang Wang, et al., "Ternary nets formed by self-assembly of triangles, squares, and tetrahedra," Angew. Chem. Int. Ed., (2005), vol. 44, pp. 2877-2880.

T, Yildirim, et al., "Direct observation of hydrogen adsorption sites and nanocage formation in metal-organic frameworks," Physical Review Letters, Nov. 18, 2005, vol. 95, 215504 pp. 1-4.

Danil N. Dybtsev, et al, "A Homochiral Metal-Organic Material with Permanent Porosity, Enantioselective Sorption Properties, and Catalytic Activity," Agnew, Chem. Int. Ed., 2006, 45, pp. 916-920.

Flachsbart, et al., "Design and fabrication of a multilayered polymer microfluidic chip with nanofluidic interconnects via adhesive contact printing," Lab-On-A-Chip, 6, 667-674, 2006.

Timothy M. Long, et al., "Water-Vapor Plasma-Based Surface Activation for Trichlorosilane Modification of PMMA," Langmuir vol. 22, No. 9, 2006, pp. 4104-4109.

Eliphas Wagner Simoes, et al., "Study of preconcentration of non-polar compounds in microchannels with constrictions," Sensors and Actuators B 115, 2006, pp. 232-239.

Ru-Qiang Zou, et al., "Strong fluorescent emission of a new fourfold-interpenetrated diamondoid metal-organic framework of zinc(II) urocanate with one-dimensional open channels," Microporous and Mesoporous Materials 91, 2006, 233-237.

Tong Ye, et al., "Ferroeletric Metal-organic framework with a high dielectric constant," JACS, 2006, 128, pp. 6554-6555.

Banglin Chen, et al., "A microporous metal-organic framework for gas-chromatographic separation of alkanes," Angew. Chem. Int. Ed. 2006, 45, 1390-1393.

Pascal D. C. Dietzel, et al., "Hydrogen adsorption in a nickel based coordination polymer with open metal sites in the cylindrical cavities of the desolvated framework," Chemical Communication, 2006, pp. 959-961.

Lei Wang, et al., "Highly stable chiral cadmium 1,2,4-benzenetricarboxylate: Synthesis, structure, and NLO and fluorescence properties," Inorganic Chemistry, vol. 45, No. 6, 2006, pp. 2474-2478.

Feng Zheng, et al., "Single-Walled Carbon Nanotube Paper as a Sorbent for Organic Vapor Preconcentration," Analytical Chemistry, 2006, vol. 78, No, 7, pp. 2442-2446.

Rasmus Damgaard Poulsen, et al., "Solvothermal synthesis, multi-temperature crystal structures and physical properties of isostructural coordination polymers, $2C_4H_{12}N^+$-$[M_3(C_8H_4O_4)_4]^{2-}$$3C_5H_{11}NO$ $M=$Co, Zn," Acta Crystallography (2006) B62, pp. 245-254.

Piotr Krawiec, et al., "Improved hydrogen storage in the metal-organic framework $Cu_3(BTC)_2$," Advanced Engineering Materials (2006) 8 No. 4, pp. 293-296.

Cameron J. Kepert, "Advanced functional properties in nanoporous coordination framework materials," Chemical Communication, (2006) pp. 695-700.

Long Pan, et al., "Separation of hydrocarbons with a microporous metal-organic framework," Angew. Chem. Int. Ed. (2006) vol. 45, pp. 616-619.

Shuangquan Zang, et al., "Interweaving of triple-helical and extended metal-o-metal single-helical chains with the same helix axis in a 3D metal-organic framework," Inorganic Chemist (2006), vol. 45, No. 10, pp. 3855-3857.

U. Mueller, et al., "Metal-organic framework—prospective industrial applications," Journal of Materials Chemistry, (2006) vol. 16, pp. 626-636.

Frank Stallmach, et al., "NMR studies on the diffusion of hydrocarbons on the metal-organic framework material MOF-5," Angew. Chem. Int. Ed. (2006), vol. 45, pp. 2123-2126.

Gyungse Park, et al., "Solvothermal synthesis, crystal structure, and magnetic properties of $[Co_3(SDA)_3(DMF)_2]$; 2-D layered metal-organic framework derived from 4,4' stilbenedicarboxylic acid $(H_2SDA)$," Bull. Korean Chem. Soc. (2006)., vol. 27, No. 3 .443-446.

Enrica Biemmi, et al "Synthesis and characterization of a new metal organic framework structure with a 2D porous system: $(H_2Net_2)$$[Zn_3(BDC_4)]$ 3DEF," Solid State Sciences 8, (2006), pp. 363-370.

Suzy Surble, et al., "An EXAFS study of the formation of a nanoporous metal-organic framework: evidence for the retention of secondary building units during synthesis," Chem Commun., (2006) pp. 1518-1520.

Cheng-Zhi Xie, et al., "A novel 3D $Cu^1$ metal-organic framework with middle-size channels despite the sixfold $ThSi_2$ interpenetrating topological structure," Eur. Journal of Inorganic Chemistry (2006) pp. 1337-1340.

Subhadip Neogi, et al., "Metal-organic frameworks of lanthanide (III) ions with a pod and bearing terminal carboxylates: Identification of water clusters of different nuclearity," Polyhedron 25 (2006) pp. 1491-1497.

C. Prestipino, et al. "Local structure of framework Cu(II) in HKUST-1 metallorganic framework: spectroscopic characterization upon activation and interaction with adsorbates," Chemical Materials, (2006), vol. 118, pp. 1337-1346.

Andrea C. Sudik, et al., "A metal-organic framework with a hierarchical system of pores and tetrahedral building blocks," Angew. Chem. Int. Ed., (2006), vol. 45, pp. 2528-2533.

Antek G. Wong-Foy, et al., "Exceptional $H_2$ saturation uptake in microporous metal-organic frameworks," Journal of the American Chemical Society (2006), vol. 128, pp. 3494-3495.

Jianghua He, et al., "Three metal-organic frameworks prepared from mixed solvents of DMF and HAc," Microporous and Mesoporous Materials, (2006), vol. 90, pp. 145-152.

Byunghoon Bae, et al., "A Touch-Mode Capacitance Microvalve Equipped with High Speed and Pressure Microsecond Switching Performance," MEMS 2006, Istanbul, Turkey, Jan. 22-26, 2006, pp. 766-769.

Patrick R. Lewis, et al., "Recent Advancements in the Gas-Phase MicroChemLab," IEEE Sensors Journal, vol. 6, No, 3, Jun. 2006, pp. 784-795.

Shaurya Prakash, et al., "Electroosmotic Flow in 'Click' Surface Modified Microfluidic Channels," Proceedings of ASME ICNMM2006, $4^{th}$ International Conference on Nanochannels, Microchannels and Minichannels, Jun. 19-21, 2006, Limerick, Ireland, Paper No. ICNMM2006-96153.

J. Yeom, et al., "Design and Characterization of Micropost-Filled Reactor for the Minimal Pressure Drop and Maximal-Surface-Area-to-Volume Ratio," Proceedings of IMECE 2006, 2006 ASME International Mechanical Engineering Congress and Exposition, Nov. 5-10, 2006, Chicago, Illinois, USA, IMECE2006-15836.

Zhuojia Lin, et al., "Microwave-Assisted Synthesis of Anionic Metal-Organic Frameworks Under Ionothermal Conditions," The Royal Society of Chemistry 2006, Chem. Commun., 2006, pp. 2021-2023.

N. Rajic, et al., "An Evidence for a Chain to Network Transformation During the Microwave Hydrothermal Crystallization of an Open-Framework Zinc Terephthalate," J. Porous Mater. 2006, vol. 13: pp. 153-156.

Ioana Voiculescu, et al., "Micropreconcentrator for Enhanced Trace Detection of Explosives and Chemical Agents," IEEE Sensors Journal, vol. 6, No. 5, Oct. 2006, pp. 1094-1104.

Bochobza-Degani, O. et al., On the effect of residual charges on the pull-in parameters of electrostatic actuators, Sensors and Actuators A 97-98:563-568 (2002).

Bosch, D. et al., A silicon microvalve with combined electromagnetic/electrostatic actuation, Sensors and Actuators 37-38:684-692 (1993).

Castañer, L. M. et al., Pull-in time—energy product of electrostatic actuators: comparison of experiments with simulation, Sensors and Actuators, 83:263-269 (2000).

Legtenberg, R. et al., Electrostatic Curved Electrode Actuators, Journal of Microelectromechanical Systems 6(3):257-265 (1997).

Messner, S. et al., 3-way silicon microvalve for pneumatic applications with electrostatus actuation principle, Microfluid Nanofluid 89-96 (2006).

Messner, S. et al., Electrostatic driven 3-way silicon microvalve for pneumatic applications, IEEE 88-91 (2003).

Oberhammer, J. et al., Design and fabrication aspects of an S-shaped film actuator based DC to RF MEMS switch, Journal of Microelectromechanical Systems 13(3):421-428 (2004).

Ohnstein, T. et al., Micromachined silicone microvalve, Proc. IEEE Micro Electro Mechanical Systems, An Investigation of Micro Structures, Sensors, Actuators, Machines and Robots, Napa Valley, CA 95-98 (1990).

Philpott, M. L. et al., Switchable electrostatic micro-valves with high hold-off pressure, Technical Digest of the 2000 Solid-State Sensor and Actuator Workshop, 226-229.

Sato, K. et al., An electrostatically actuated gas valve with an S-shaped film element, J. Micromech. Microeng. 4:205-209 (1994).

Schaible, J. et al., Electrostatic microvalves in silicon with 2-way-function for industrial applications, The $11^{th}$ International Conference on Solid-State Sensors and Actuators, Munich, Germany 928-931 (2001).

Shikida, M. et al., Characteristics of an electrostatically-driven gas valve under high-pressure conditions, Center for Materials Processing Technology 235-240 (1994).

Shikida, M. et al., Electrostatically driven gas valve with high conductance, Journal of Microelectromechanical Systems, 3(2):76-80 (1994).

Shikida, M. et al., Fabrication of an S-shaped microactuator, Journal of Microelectromechanical Systems, 6(1):18-24 (1997).

Shikida, M. et al., Micromachined S-shaped actuator, Sixth International Symposium on Micro Machine and Human Science 167-172 (1995).

Shikida, M. et al., Response time measurement of electrostatic S-shaped film actuator related to environmental gas pressure conditions, IEEE 210-215 (1996).

Vandelli, N. et al., Development of a MEMS microvalve array for fluid flow control, Journal of Microelectromechanical Systems 7(4):395-403 (1998).

Yang, X. et al., An electrostatic, on/off microvalve designed for gas fuel delivery for the MIT microengine, Journal of Microelectromechanical Systems, 13(4):660-668 (2004).

Huff et al., A pressure-balanced electrostatically-actuated microvalve, Technical Digest, 1990 Solid-State Sensor and Actuator Workshop, pp. 123-127 (1990).

* cited by examiner

Panel A

Panel B

Panel C

Panel D

Panel A

Panel B

MICROMACHINED GAS CHROMATOGRAPHY COLUMNS FOR FAST SEPARATION OF ORGANOPHOSPHONATE AND ORGANOSULFUR COMPOUNDS AND METHODS FOR DEACTIVATING SAME

CROSS-REFERENCES TO RELATED APPLICATIONS

This application claims priority to and benefit under 35 U.S.C. §119(e) to U.S. Provisional Application Ser. Nos. 61/021,588 and 61/021,620, both filed Jan. 16, 2008, the disclosures of which are herein incorporated by reference in their entirety herein.

STATEMENT AS TO RIGHTS TO INVENTIONS MADE UNDER FEDERALLY SPONSORED RESEARCH OR DEVELOPMENT

This invention was made, at least in part, with U.S. government support under the Defense Advanced Research Projects Agency (DARPA) under U.S. Air Force Grant FA8650-04-1-7121. The Government has certain rights in this invention.

BACKGROUND OF THE INVENTION

1. Field of the Invention

The invention relates generally to columns and methods for producing microcolumns suitable for use in gas chromatographs. In particular, following deposition of the stationary phase coating, the microcolumns are subjected to a postcoating treatment with a molecule that binds to the active sites in the stationary phase column thereby reducing or eliminating loss of gas chromatograph performance associated with those active sites.

2. Related Art

A gas chromatograph (GC) is a chemical analysis instrument used for separating chemicals in a complex sample and is generally composed of three basic parts, an injector, a column, and a detector. Different chemical constituents of a sample pass in a gas stream through the column at different rates depending on their various chemical and physical properties and their interaction with a specific column filling, called the stationary phase. As the chemicals exit the end of the column, they are detected and identified electronically. Conventional GC columns are generally small open tubes with internal diameters in the range of about 270 microns to about 530 microns and lengths in the range of about 10 meters to 30 meters. The inside walls of these columns are coated with a thin even layer of organic polymer, the GC liquid phase, to a thickness of less than about one micron.

Microfabricated gas chromatograph (μGC) column development has received considerable interest for the analysis of toxic chemicals, explosives, disease markers and other analytes. In general, column fabrication starts with first etching microfluidic channels in a silicon or glass wafer and then sealing the etched microfluidic channels using anodic or fusion bonding. The microcolumn walls are then deactivated. Subsequently, static or dynamic coating techniques may be used to deposit the stationary phase inside the microcolumn prior to analyte analysis.

Many studies have reported columns that can separate hydrocarbons and a few studies have reported microfabricated columns that are able to show significant separation of organophosphonates. In the organophosphonate separation studies, however, the organophosphonate peaks exhibit significant tailing due to unwanted adsorption to the active sites present in the microcolumn. FIG. 1 shows a fast μGC chromatogram, however, most noteworthy is that the dimethyl methyl phosphonate (DMMP), diethyl methyl phosphonate (DEMP), and diisopropyl methyl phosphonate (DIMP) peaks tail, which makes the microcolumns less than optimal for fast portable GC. Accordingly, there is a need for improved deactivation of the walls of columns, particularly in microcolumns suitable for use in GCs and μGCs.

BRIEF SUMMARY OF THE INVENTION

The invention provides improved microcolumns and methods for producing microcolumns having enhanced GC performance. In one aspect, following deposition of the stationary phase, the microcolumns are subjected to post-treatment with a molecule that binds to the active sites in the stationary phase, thereby reducing or eliminating loss of GC performance associated with those active sites.

According to one aspect of the invention, a method for preparing a gas chromatograph (GC) column may include deactivating a plurality of walls of a GC column, depositing a stationary phase in the GC column, and treating the GC column with a molecule such that the molecule binds to active sites in the stationary phase of the column.

The deactivating step may employ a method such as silylation, perisilylation, and deactivation using an organosilicon hydride, for example. Specifically, the silylation may be performed using DMDCS, the perisilylation may be performed using Ah3P, and the deactivation with the organosilicon hydride may be performed using DPTMDS.

The postcoating molecule may be an acid including hydrocarbon ligands, a base including hydrocarbon ligands, a thiol, a phosphine, and/or an amine. Moreover, the postcoating molecule may be a structure of Formula I:

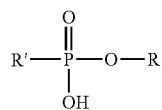

Formula 1 where r and r' are linear branched or substituted hydrocarbons. More specifically, the postcoating molecule may be the structure of Formula II:

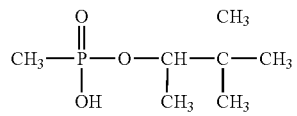

Formula 2

In another aspect according to the invention, a gas chromatograph (GC) column prepared by the methodology of the invention may include deactivating a plurality of walls of a GC column, depositing a stationary phase in the GC column, and treating the GC column with a molecule such that the molecule binds to active sites in the stationary phase of the column. The stationary phase may be applied at a pressure of about 0.9 psi and at a concentration of about 10 w/v %.

The GC column may include a postcoating molecule having a structure of Formula III:

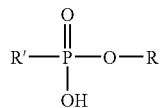

Formula 1 where R and R' are linear branched or substituted hydrocarbons. Specifically, the GC column may include a molecule having the structure of Formula II:

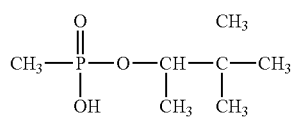

Formula 2

The GC column may include a postcoating molecule having the structure of Formula III:

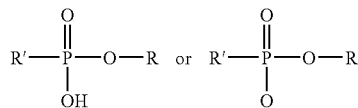

Formula 3 where R and R' are linear branched or substituted hydrocarbons.

According to one aspect of the invention, a GC column may include a plurality of column walls each having a deactivated inner surface, a stationary phase layer deposited on the deactivated inner surface of the column walls, a plurality of binding sites in the stationary phase layer, and a post-coating molecule bound to at least one of the binding sites in the stationary phase layer. The inner surface of the column walls may be deactivated with a compound selected from the group consisting of DMDCS, Ah3P, and DPTMDS. The stationary phase layer may have a thickness of about 0.1 μm and may be uniformly spread over the inner surface of said plurality of column walls. The column walls may have a serpentine configuration. The column walls may be rounded.

The post-coating molecule may have a structure of Formula I:

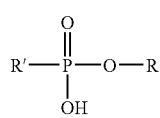

Formula 1 where R and R' are linear branched or substituted hydrocarbons.

The post-coating molecule may have the structure of Formula II:

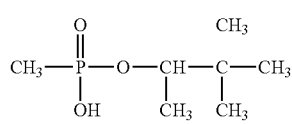

Formula 2

The post-coating molecule may have the structure of Formula III:

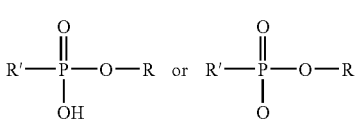

where R and R' are linear branched or substituted hydrocarbons.

The post-coating molecule may be one or more compounds such as a thiol, a phosphine, and an amine.

Additional features, advantages, and embodiments of the invention may be set forth or apparent from consideration of the following detailed description, and claims. Moreover, it is to be understood that both the foregoing summary of the invention and the following detailed description are exemplary and intended to provide further explanation without limiting the scope of the invention as claimed.

BRIEF DESCRIPTION OF THE DRAWINGS

The accompanying drawings, which are included to provide a further understanding of the invention, are incorporated in and constitute a part of this specification, illustrate embodiments of the invention and together with the detailed description serve to explain the principles of the invention. No attempt is made to show structural details of the invention in more detail than may be necessary for a fundamental understanding of the invention and various ways in which it may be practiced.

DETAILED DESCRIPTION OF THE INVENTION

Figure 1:
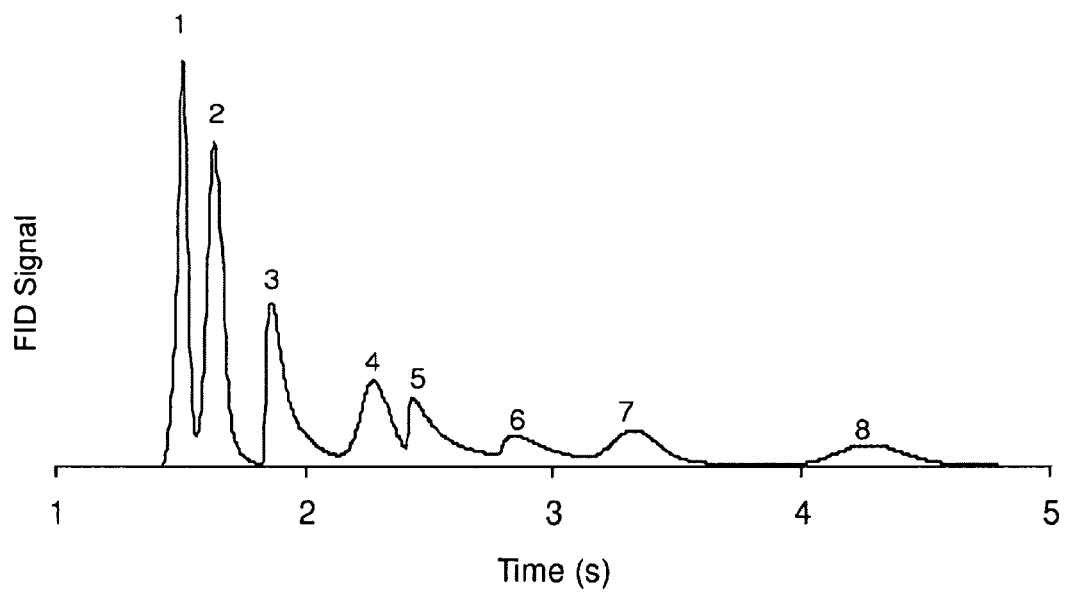
FIG. 1 is a chromatogram showing a 4 second separation obtained in the conventional OV-5 coated microcolumn. The separation was obtained by 1 μl headspace injection with a split of 100:1, column inlet pressure held at 25 psi and oven temperature ramped from 90° C. to 98° C. at 12° C./min. Hydrogen was used as the carrier gas. Peaks represent (1) ethyl ether, (2) Toluene, (3) dimethyl methyl phosphonate, (4) diethyl methyl phosphonate, (5) n-octanol, (6) diisopropyl methyl phosphonate, (7) 1,6-dichlorohexane, and (8) dodecane. Notable is that the dimethyl methyl phosphonates, diethyl methyl phosphonate, octanol and diisopropyl methyl phosphonates peaks tail, leading to an apparent non-zero baseline between 2 and 3.3 seconds.

It is understood that the invention is not limited to the particular methodology, protocols, and reagents, etc., described herein, as these may vary as the skilled artisan will recognize. It is also to be understood that the terminology used herein is used for the purpose of describing particular embodiments only, and is not intended to limit the scope of the invention. It also is noted that as used herein and in the appended claims, the singular forms "a," "an," and "the" include the plural reference unless the context clearly dictates otherwise. Thus, for example, a reference to "a bend" is a reference to one or more bends and equivalents thereof known to those skilled in the art.

Unless defined otherwise, all technical and scientific terms used herein have the same meanings as commonly understood by one of ordinary skill in the art to which the invention pertains. The embodiments of the invention and the various features and advantageous details thereof are explained more fully with reference to the non-limiting embodiments and examples that are described and/or illustrated in the accompanying drawings and detailed in the following description. It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments of the invention. The examples used herein are intended merely to facilitate an understanding of ways in which the invention may be practiced and to further enable those of skill in the art to practice the embodiments of the invention. Accordingly, the examples and embodiments herein should not be construed as limiting the scope of the invention, which is defined solely by the appended claims and applicable law. Moreover, it is noted that like reference numerals reference similar parts throughout the several views of the drawings.

Accordingly, provided immediately below is a "Definition" section, where certain terms related to the invention are defined specifically for clarity, but all of the definitions are consistent with how a skilled artisan would understand these terms. Particular methods, devices, and materials are described, although any methods and materials similar or equivalent to those described herein can be used in the practice or testing of the invention. All references referred to herein are incorporated by reference herein in their entirety.

DEFINITIONS

Ah3P is Phenyltris(dimethylsiloxy)silane
BOE is Buffered Oxide Etching
DMDCS is Dimethyldichlorosilane
DEMP is Dimethyl Methyl Phosphonate
DIMP is Diisopropyl Methyl Phosphonate
DMMP is Dimethyl Methyl Phosphonate
DPTMDS is Diphenyltetramethyl Disilazane
DRIE is Deep Reactive Ion Etching
FTIR is Fourier Transform Infrared Spectroscopy
GC is Gas Chromatograph
HF is Hydrofluric Acid
HMDS is Hexamethyldisilazane
KOH is Potassium Hydroxide
µGC is Microfabricated Gas Chromatograph
OP is Organophosphonate
OS is Organosulfur
OV-5 is 5% diphenyl 95% dimethylpolysiloxane
PMP is Pinacolymethyl Phosphonate
$SiO_2$ is Silicon Dioxide The invention relates generally to columns and methods for preparing columns for use in µGCs and also conventional GCs, which result in sharp μGC or GC peaks on chromatographs, with relatively little or no peak tailing characteristics. In particular, the microcolumns of the invention following stationary phase coating may be subjected to a post-coating treatment with a molecule that strongly binds to the active sites in the stationary phase column thereby "deactivating" the active sites associated with the stationary phase and reducing or eliminating the loss of μGC performance or GC performance associated with those active sites. The molecule should bind strongly to the same active sites as the analytes of interest and may be or the same or heavier molecular weight. The molecule, however, has to be fairly volatile so it does not contaminate the stationary phase. Specifically, for example, the microcolumn may be postcoated with an alkylating phosphonate. The alkylating phosphonate functions by deactivating sites in the stationary phase that cause phosphonate peaks to tail "permanently."

According to one embodiment of the invention, the microcolumns of the invention may be produced by employing the following fabrication sequence: (i) etching microfluidic channels in a substrate; (ii) employing anodic or fusion bonding to seal the etched microfluidic channels to create microcolumns; (iii) deactivating the microcolumn walls; (iv) depositing the stationary phase within the microcolumns by employing static or dynamic coating; and (v) post-treating with a molecule that binds with the active sites within the stationary phase.

Figure 2:
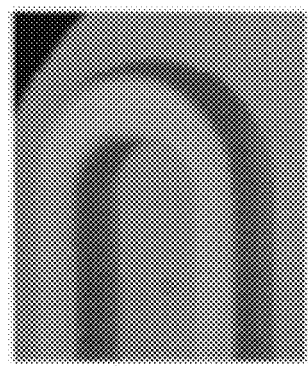
FIG. 2: are photographs showing bend geometries that may be used for constructing the analytical columns according to principles of the invention. Panel A is a photograph showing circular bends. Panel B is a photograph showing sine wave bends. Panel C is a photograph showing conically converging bends. Panel D is a photograph showing concentrically converging bends.
Figure 2:
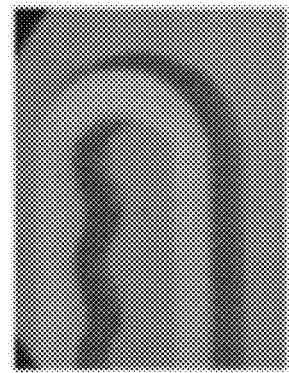
Figure 2:
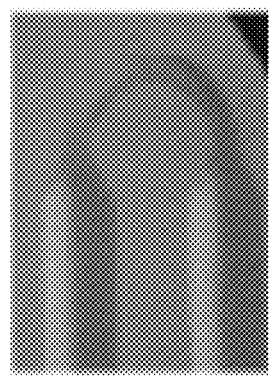
Figure 2:
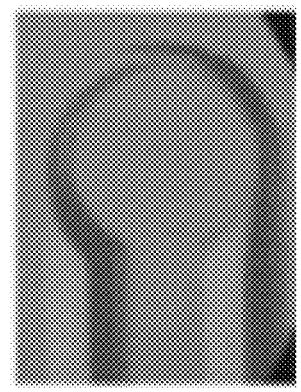
Figure 3:
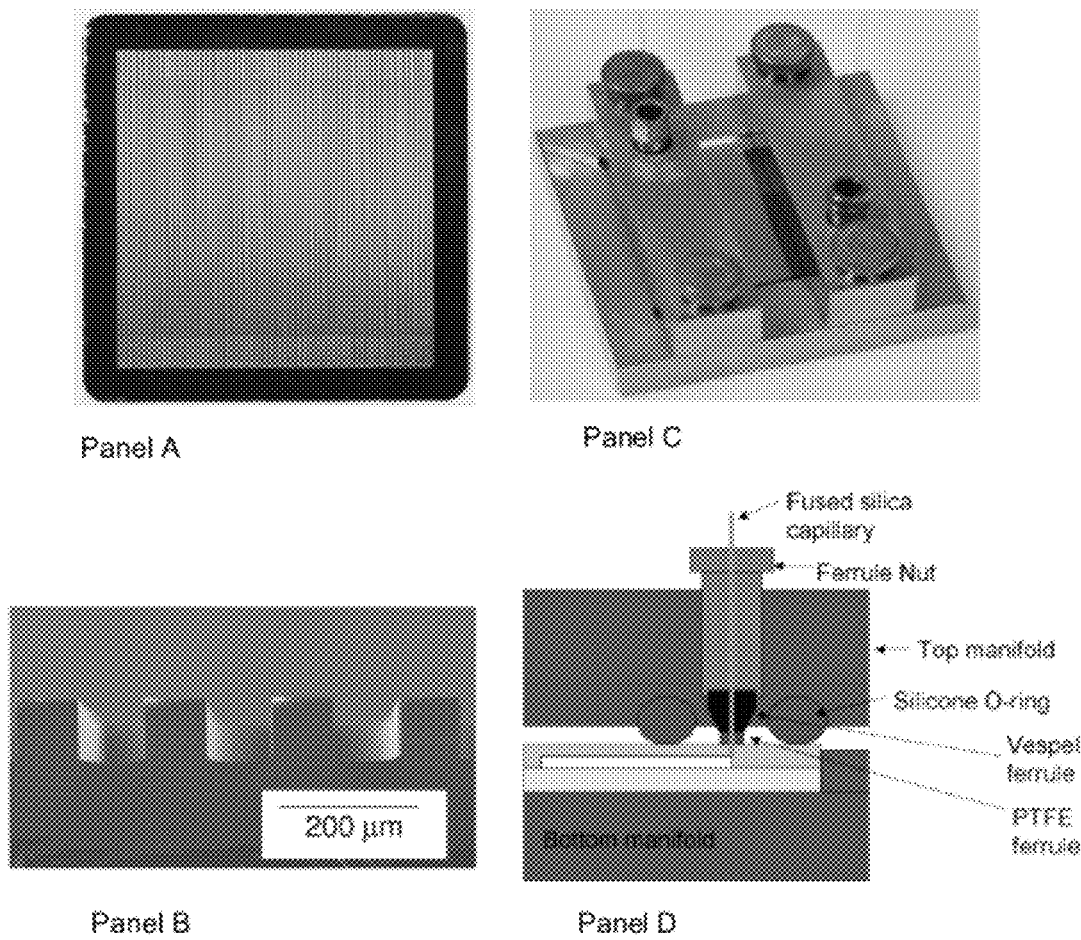
FIG. 3: Panel A is a photograph showing a 3 meter long micromachined serpentine column on a 3.2 cm square and 500 μm thick silicon piece anodically bonded to 1 mm thick Pyrex 7740®, constructed according to principles of the invention. Capillaries were attached to the back of the column using an in-house made manifold as indicated in FIG. 1D. Restek (#560292) deactivated guard columns (I.D. 200 μm, O.D. 100 μm) were used to make all connections. Panel B is a scanning electron micrograph of 100 μm wide and 100 μm deep channels, constructed according to principles of the invention. Panel C is a photograph of brass manifold packaging for a microcolumn produced by principles of the invention. Panel D is a schematic showing details of a low dead volume connection to the microcolumn constructed according to principles of the invention.

The microfluidic channels of the invention may be fabricated by etching the surface by employing deep reactive ion etching (DRIE), Bosch, or other etching processes appropriate for forming the desired microfluidic channel structure in the material of the substrate or the wafer. Other suitable fabrication techniques known by those of skill in the art may include mechanical machining or laser milling, embossing or molding of polymeric compositions, photo-lithography of UV-curable polymer compositions, and photoforming layers. In a particular aspect, the columns may be constructed using advantageous channel architectures, such as a serpentine channel structure, spiral channel structure, or rectangular channel structure. Moreover, the serpentine channel structure may be constructed to exhibit various bend geometries for enhancing μGC separation, as disclosed in U.S. Appln. No. 61/021,588. The geometric bends may include circular bends (FIG. 2, Panel A), sine wave bends (FIG. 2, Panel B), conically converging bends (FIG. 2, Panel C), and concentrically converging bends (FIG. 2, Panel D), for example. Substrates or wafers that may be employed in the invention may be any suitable material such as silicon, glass, polyimide, silicon carbide, nickel, and other materials that are easy to fabricate. For example, etching and sealing of the microfluidic channels may be accomplished by the exemplary procedures described in Preparatory Example 1, below. FIG. 3 shows images of a microfabricated column of the invention prepared by the procedures described in Preparatory Example 1. FIG. 3 shows a microcolumn having a series of 100 microns wide, 100 microns deep channels on a 3.2×3.2 cm silicon wafer arranged in a serpentine pattern.

The microcolumns of the invention may have a diameter in the range of about 20 microns to about 1000 microns, and specifically in a range of about 25 microns to 250 microns, and more specifically in the range of about 25 microns to about 50 microns. The columns may have a depth in the range of about 20 microns to about 600 microns, and specifically in the range of about 50 to about 250 microns. The microcolumns may have a length in the range of about 0.3 meters to about 50 meters, and in particular, a length of about 1 to 10 meters. The spacing between adjacent channels may be less than about 4 times the microcolumn channel diameter, and specifically may be in the range of about 30 microns to about 200 microns In one particularly advantageous embodiment of the invention, the microcolumns may be about 3 meters long, about 100 microns wide, about 100 microns in depth, and have about 100 micron spacing between channels.

The etching process used to fabricate the channels structures of the invention, however, may undesirably generate scallops, indentations, or rough edges in the walls of the channels. The rough edges may be undesirable because they may interfere with attaining an uniform stationary phase deposition and ultimately effect the resolution of the GC by causing band broadening. Therefore, according to a further aspects of the invention, the methodology may further include smoothening the channel walls by employing a buffered ion etching (BOE) or an anodization process as disclosed in U.S. Appln. No. 61/021,588.

As appreciated by those of skill in the art, BOE, also known as buffered HF or BHF, is a wet etchant used in microfabrication. Its primary use is in etching thin films of $SiO_2$ or silicon nitride ($Si_3N_4$). In general, BOE comprises a mixture of a buffering agent, such as ammonium fluoride ($NH_4F$), and HF. A common BOE solution may comprise a 6:1 volume of about 40% $NH_4F$ in water to about 49% HF in water, which will etch thermally grown oxide at approximately 2 nm/s at 25° C. BOE is used to remove $SiO_2$ and is a very selective etch because it stops etching at the silicon and does not etch any further. In a specific aspect, a substantially even wet oxide layer having a thickness of about 2 mm may be grown on the DRIE channel walls in silicon and may be subsequently smoothened by BOE to remove the wet oxide completely.

In another embodiment, the DRIE channel walls may be smoothened by employing anodization. Anodization is a standard electrochemical technique known by those skilled in the art for making porous silicon and involves the application of a potential to a bulk silicon sample or silicon wafer. The silicon wafer may be immersed in an electrolyte solution which is commonly a mixture of HF, water and other components. The silicon wafer is held positive and a platinum mesh is used a negative electrode. In one specific aspect, porous silicon may be grown using anodization and subsequently etched using a mild potassium hydroxide (KOH) solution. The silicon anodization may take place at 0.25 A/cm$^2$ in a 1:1 HF and ethanol electrolytic bath. Typical mild KOH concentrations may include molar solutions in the range of about 5 molar to about 10 molar.

In another embodiment, the DRIE channels may be rounded by dynamically coating a glass layer. In this process, a glass deposition solution (e.g., spin on glass from Filmtronics (P120F and 550F, for example) or Honeywell (512B, for example)) is used to coat channel surface. Thicker later of glass may be deposited in the corners, which avoids pooling of stationary phase in the subsequent process of coating a stationary phase.

In a further embodiment, the rounded micro-columns may be created by using buried structure channels (BSC). BSC may be created by etching the channels first with a DRIE, followed by a wall protection with silicon dioxide and the last step of iso-etching with SF6 RIE. This process results in partially buried micro-columns with minimum corners and hence even deposition of stationary phase when coating them.

In one embodiment of the invention, the channel walls may be smoother than about one order of magnitude less than the phase thickness. For example, if the phase thickness is about 400 nm, then the channel walls should have a smoothness of about 40 nm or if the phase thickness is 100 nm, then the channel walls should have a smoothness of about 10 nm.

Moreover, the etching process may also create undesirable sharp bends in the channel structure, which may cause the stationary phase to build up in the corners of the bends and negatively effect the resolution of the μGC. Therefore, if desired, the radius of the bend may be reduced by rounding off the bottom of the bend in the channel structure to promote uniform phase coating as disclosed in U.S. Appln. No. 61/021,588.

According to one embodiment, the radius of the corner of the bend may be at least about 10 times larger than the phase thickness, thus with about a 400 nm phase thickness, the corners should have a radius of greater than about 4 microns. The corners of the bends may be rounded off chemically using the anodization procedure described above, by machining or molding, or by coating with a suitable polymer or glass.

In one embodiment of the invention, the etched microchannels may be sealed by anodic or fusion bonding. In anodic bonding, the silicon and Pyrex© 7740 glass pieces are cleaned using RCA1 clean process, brought in surface contact, heated to 450-500° C., and applied a bias of 800-1200V. In fusion bonding the two cleaned silicon surfaces are brought in contact and heated in a furnace tube at 1100° C. Micromachined columns are commonly made of trenches in silicon. The surface of silicon is usually p or n doped, and therefore the surface may be doped with impurities and terminated with hydroxyl groups. The micromachines columns are usually sealed with Pyrex®. The Pyrex® may be engineered to form an anodic bond with silicon and match the coefficient of thermal expansion with silicon. Anodic bonding may be performed at about 1000 V and in a range of about 400° C. to about 500° C. The anodic bonding mechanism explains the flow of metal positive ions especially sodium when high electric field is applied during bonding process. The high temperature reduces the resistance to ion diffusion within Pyrex®. Therefore, such microcolumns may contain high ion contents near the Pyrex© surface as compared to silicon or conventional fused silica columns.

According to another embodiment of the invention, the sealed microcolumn walls may be deactivated prior to deposition of the stationary phase. Deactivation of fused silica columns is very well studied. Since fused silica itself is an inert material, it requires less surface modification thereby allowing stationary phase deposition. The microcolumn may be deactivated by utilizing silylation using DMDCS, perilsilyation using Ah3P, and/or deactivation with an organosilicon hydride such as DPTMDS, for example. Exemplary deactivation procedures using silyation, perilsilyation, and organosilicon hydride deactivation is described in Preparatory Example 2, below.

Figure 4:
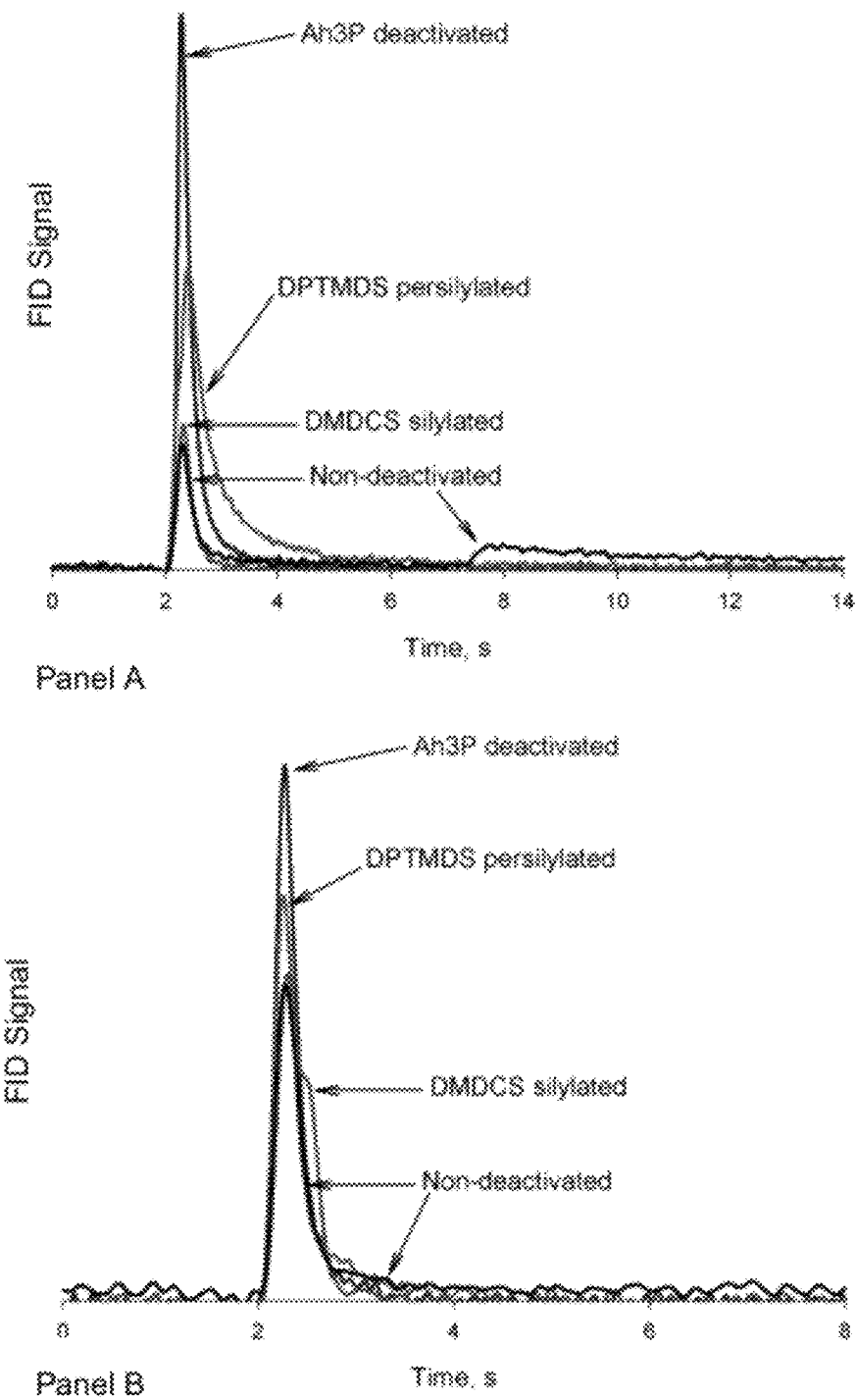
FIG. 4 shows two chromatographs. Panel A is a chromatograph comparing diisopropyl methyl phosphonate injections on a non-coated nondeactivated silicon microcolumn, a persilylated microcolumn constructed according to principles of the invention, a DMDCS silyated microcolumn constructed according to principles of the invention, and a Ah3P treated microcolumn constructed according to principles of the invention. Panel B is a chromatograph comparing n-octanol injections on a non-coated nondeactivated silicon microcolumn, a persilylated microcolumn constructed according to principles of the invention, a DMDCS silyated microcolumn constructed according to principles of the invention, and a Ah3P treated microcolumn constructed according to principles of the invention. 5 µl headspace of sample was injected on 35 cm long microcolumns with a split of 50:1 and oven temperature and inlet pressure held at 75° C. and 5 psi respectively. Hydrogen was used as the carrier gas.

FIG. 4 (Panels A and B) shows how three different deactivation procedures of the invention silylation, persilylation, and Ah3P treatment affect the DIMP (FIG. 4, panel A) and n-octanol (FIG. 4, Panel B) peaks. As shown in FIG. 4, Panel A, the DIMP injection on non-deactivated microcolumn resulted in two peaks, a small sharper peak at 2.4 seconds and a heavily tailing peak at 7.8 seconds. DIMP injection on microcolumns silylated with DMDCS resulted in only one slightly sharper peak at 2.4 seconds (FIG. 4, Panel A). DIMP injection on microcolumns perilyated with DPTMDS resulted in one big peak at 2.7 seconds (FIG. 4, Panel A). This DIMP peak, however, has a half peak width of 0.9 seconds and a strong tailing characteristic (FIG. 4, Panel A). The DIMP injections on the microcolumn deactivated with Ah3P resulted in a sharp peak at 2.4 seconds with a peak width of 0.4 seconds, with little or no tailing characteristic (FIG. 4, Panel A).

The presence of the two peaks in the non-deactivated microcolumn may be due to the saturation and desaturation of reversible phosphonate binding sites. Sample loss occurs via irreversible binding of the phosphonates. Activity test results for deactivated microcolumns showed improvement over non-deactivated microcolumns. DMDCS silylation eliminated the reversible phosphonate binding sites and only showed one DIMP peak. DPTMDS persilylation produced better response and hence better deactivation to DIMP injection compared to DMDCS silanization treatment. This occurred because persilylation produces a denser film over the surface than silylation, and thereby lower gas permeability towards the surface of the microcolumn. For DPTMDS and Ah3P deactivations, Ah3P deactivation blocked the reversible and irreversible phosphonate binding sites more efficiently and produced better deactivation than DPTMDS, and accordingly, the Ah3P deactivated microcolumn had a better response to DIMP injection than the DPTMDS deactivated microcolumn.

As shown in FIG. 4, Panel B, n-octanol injection on a non-deactivated microcolumn resulted in a peak at 2.4 seconds with strong tailing characteristics. No additional peaks were observed with n-octanol injections as were with the DIMP injections shown in FIG. 4, Panel A, described above. The n-octanol injections on the DMDCS silylated microcolumn resulted in a peak at 2.45 seconds with a slightly higher peak height and a shoulder (FIG. 4, Panel B). This peak showed less tailing characteristics compared to the non-deactivated microcolumns. The n-octanol peak on the DPTMDS persilylated microcolumn resulted in a peak at 2.35 seconds and had a higher peak height and peak area compared to silylated and non-deactivated microcolumns (FIG. 4, Panel B). The n-octanol peak on the Ah3P deactivated microcolumn resulted in a peak at 2.4 seconds and showed the highest peak height amongst all the deactivations, with little or no tailing characteristics (FIG. 4, Panel B).

The n-octanol injections on the non-deactivated column exhibited heavy tailing and did not produce two peaks as with the DIMP injections. This indicated the presence of other active sites beside hydrogen binding sites, which actively adsorb phosphonates and do not adsorb n-octanol. The DMDCS silylated microcolumn produced a peak with slightly higher peak height and reduced peak tailing compared to peaks eluted from non-deactivated columns. The DPTMDS persilylated microcolumn and Ah3P deactivation produced higher levels of deactivation. As seen in FIG. 4, Panel B, the Ah3P deactivated microcolumn resolution was the best. The results shown in FIG. 4, Panels A and B, indicate that DIMP headspace injection was a very sensitive tracer for phosphonate binding sites in the microcolumn compared to n-octanol.

Accordingly, as shown in FIG. 4, Panel A and Panel B, Ah3P deactivation surprisingly renders the non-deactivated microcolumn surface more inert to organophosphonate and sulfur compounds, compared to persilylation and silylation methods of deactivation. Also, diisopropyl methyl phosphonate was found to be a better tracer for microcolumn activity towards organophosphonates compared to n-octanol.

According another embodiment, the inside surfaces of the microcolumns may be coated with a stationary phase material to enhance the separation of the chemical analytes of interest in the gas mixture to be analyzed. The stationary phase material may be a polymer having a specific chemical group with the proper physico-chemical interaction to cause separation of the analytes. Suitable stationary phase materials are generally known by those of skill and the art and may be purchased from Agilent (HP-1 ms, DB-1 ms, HP-1, DB-1, HP-5 ms, DB-5, HP-5, DB-5 ms, DB-1301, DB-35, HP-35, DB-35 ms, DB-1701, DB-1701P, for example) Alltech (AT-1 ms, At-1ht, At-20, At-FAME, At-CAM, At-Amino Acid, AT-Sulfur, for example), or Restek (Rtx/MXT-1, Rtx/MTX-1301, Rtx/MXT/XTI-5, for example). The microcolumns may be coated with the stationary phase material by a number of methods known by those skilled in the art. Methods may include, for example, filling the column with a solvent containing the stationary phase material and then applying a vacuum to the end of the column to dry the solvent out of the column, or by using sol-gel techniques, static techniques, or dynamic techniques. The thickness of the stationary phase may be about 0.1 µm, uniformly spread over the inner surface of the microcolumn with minimum or no pooling. Exemplary procedures for stationary phase coating are described in Preparatory Example 3, below.

According to another embodiment, the microcolumns may be post-treated after stationary phase deposition with a molecule that binds to the active sites in the stationary phase microcolumn. As described above, the molecule should bind to the same active sites as the analytes of interest, but should be substantially volatile so it does not contaminate the stationary phase. Additionally, the postcoating molecule may be of equal or greater molecular weight than the analyte of interest. Exemplary procedures for post-coating the microcolumn are described in Preparatory Example 4, below.

In one embodiment, if the analyte of interest is an organophosphonate (OP) or organosulfur (OS), the post-treatment molecule may have a structure of Formula I:

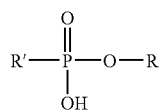

Formula 1 where R and R' are linear branched or substituted hydrocarbons that would also poison the base sites in the stationary phase. Commercially available compounds may include ethyl-methyl phosphonate (CAS 1832-53-7), cyclohexyl hydrogen methylphosphonate (CAS 1932-60-1) isopropyl methylphosphonic acid (CAS 1832-54-8) and pinacolyl methylphosphonate (PMP) (CAS 616-52-4), for example.

In a specific embodiment, pinacolyl methylphosphonate (PMP) (CAS 616-52-4) having a structure of Formula II, below, may be used to post-treat the microcolumn:

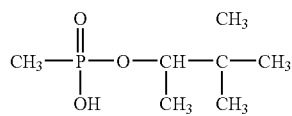

Formula 2

Depending upon the analyte of interest, additional post-treatment molecules may include OS, thiols for the Lewis base sites, and phosphines for acid sites, and amines for acid sites.

Figure 5:
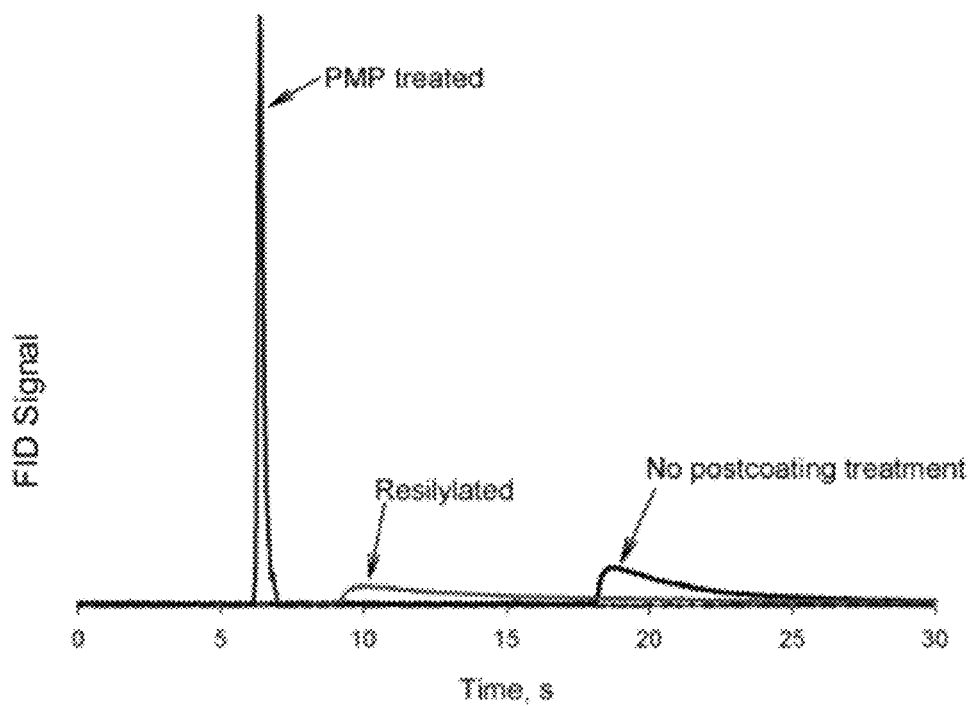
FIG. 5 is a chromatograph comparing injections for diisopropyl methyl phosphonate headspace injection on a Ah3P deactivated and a OV-5 coated microcolumn without further treatment, and with further heat treatment with re-silylating agent (Rejuv-8®) according to principles of the invention and with pinacolyl methylphosphonate according to principles of the invention. The analysis was carried out on coated 3 meter long microcolumns by injecting 5 µl headspace with a split of 50:1 and oven temperature and inlet pressure held at 120° C. and 10 psi respectively. Hydrogen was used as the carrier gas.

FIG. 5 shows effects of two post-coating treatments: resilylation and PMP treatment on Ah3P deactivated microcolumns. DIMP injections on a no-postcoating microcolumn resulted in a peak at 18.1 seconds and exhibited strong tailing characteristics. The Rejuv-8 (Sigma Aldrich, St. Louis, Mo.) resilylated microcolumn resulted in faster elution of the DIMP at 9.8 seconds. This DIMP peak was smaller in height and exhibited stronger tailing characteristics compared to the no-postcoating treatment microcolumn. PMP treatment of the microcolumn decreased the retention time of DIMP peak to 6.7 seconds. This DIMP peak was much sharper, slightly asymmetric and showed little or no tailing characteristics. The peak width at half height of the DIMP peak was 0.15 seconds.

The effect of post-coating treatment on phosphonate activity was carried out on 3 meter long, OV-5 coated, Ah3P deactivated microcolumns. DMMP (Sigma Aldrich, Santa Clara, Calif.), DEMP (Sigma Aldrich, Santa Clara, Calif.), DIMP, TEP (Sigma Aldrich, Santa Clara, Calif.) were the organophosphonates and isopropyl sulfide (IPS) (Sigma Aldrich, Santa Clara, Calif.), chloroethyl methyl sulfide (CEES) (Sigma Aldrich, Santa Clara, Calif.), and isopropyl sulfonyl chloride (IPSC) (Fluka, Santa Clara, Calif.) were the organosulfur compounds used in this study. A mix comprising of reagents listed in Table 1, immediately below was prepared.

TABLE 1

| No. | Compound |
|---|---|
| 1 | 2-chloro-2-methylpropane |
| 2 | Ethyl ether |
| 3 | Isooctane |
| 4 | Diisopropyl sulfide |
| 5 | Chloroethyl methyl sulfide |
| 6 | Nonane |
| 7 | Dimethyl methyl phosphonate |
| 8 | Isopropane sulfonyl chloride |
| 9 | Decane |
| 10 | Diethyl methyl phosphonate |
| 11 | Diisopropyl methyl phosphonate |
| 12 | Undecane |
| 13 | Triethyl phosphate |
| 14 | Menthone |
| 15 | Isoborneal |
| 16 | Dodecane |

Figure 6:
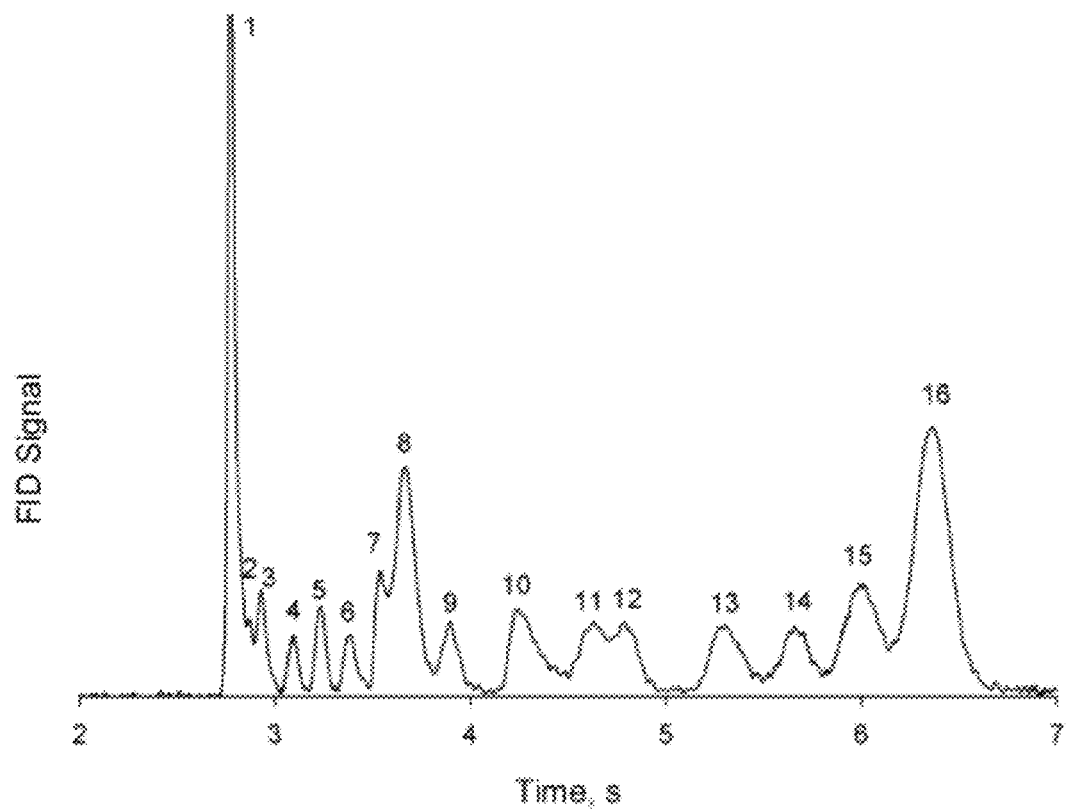
FIG. 6 is a chromatograph showing the separation of phosphonate and sulfur compounds described in Table 2 on the pinacolyl methyl phosphonate treated microcolumn of the invention. Testing was carried out using hydrogen as carrier gas. 1 µl headspace of the mix was injected with a split of 120:1, the oven temperature held at 110° C. and inlet pressure ramped from 35 psi to 45 psi at the rate of 150 psi/min.

FIG. 6 shows the separation of an OP and sulfur compound mix (described in Table 1, above) on a PMP postcoated, Ah3P deactivated microcolumn of the invention. The numbers in Table 1, above, correspond to the numbered peaks in FIG. 6. As shown in FIG. 6, the fast GC chromatogram shows easily resolvable and less tailing peaks of OP (peaks 7, 10, 11, 13) and OS compounds (peaks 4, 5, 8). Peak 10 corresponding to diethyl methylphosphonate (DEMP) shows an assymetric peak having some residual activity. The separation of compounds was obtained within a 4 seconds long window.

Figure 7:
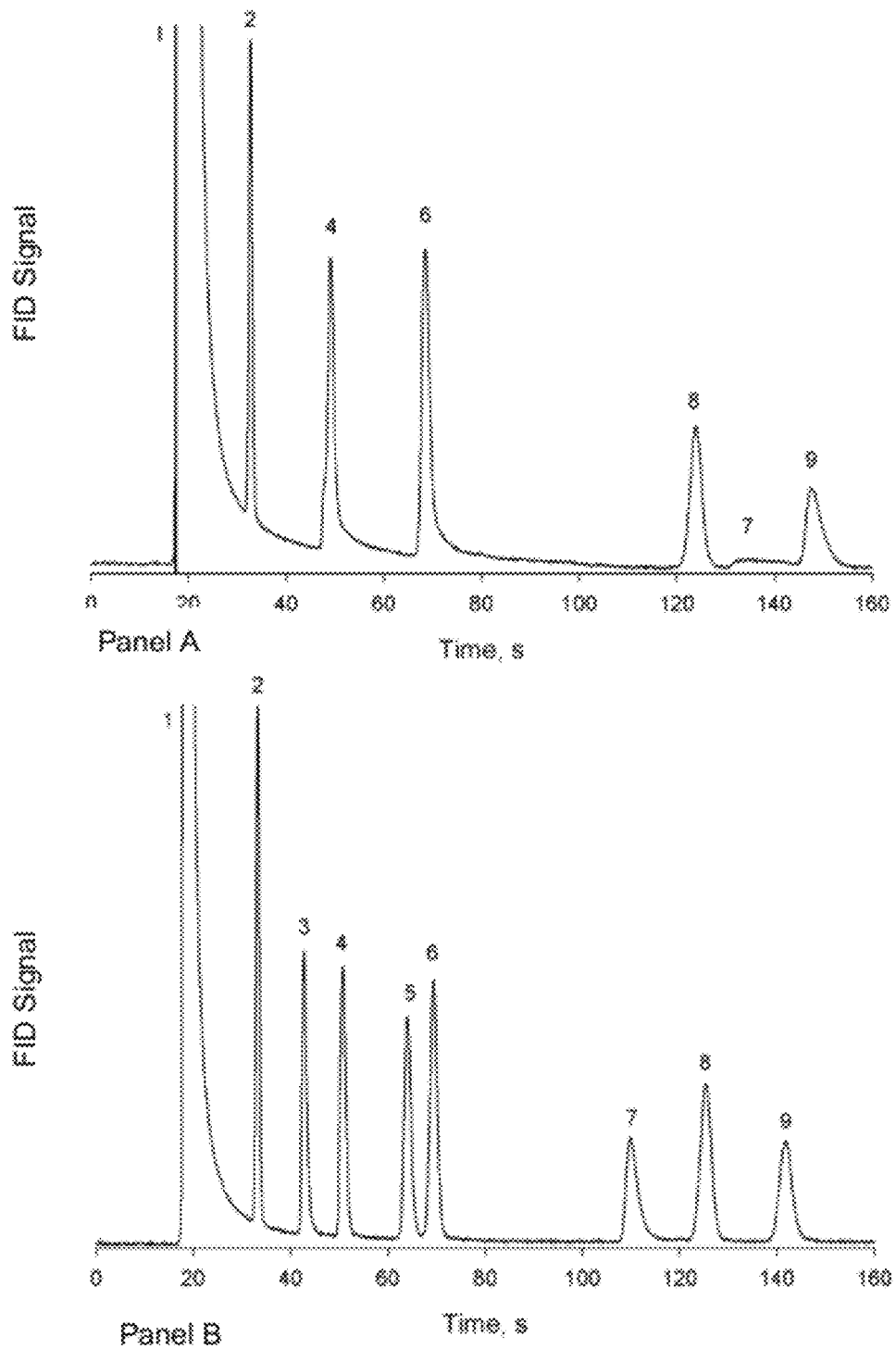
FIG. 7 shows two chromatographs of column test mix injections. Panel A is a chromatograph of column test mix injections on Ah3P deactivated and OV-5 coated without PMP treatment. Panel B is a chromatograph of column test mix injections on Ah3P and OV-5 coated with PMP treatment according to principles of the invention. 1 µl of test mix liquid was injected with a split of 1000:1, column temperature held at 120° C. and inlet pressure adjusted to achieve a helium carrier gas velocity of 20 cm/s.

FIG. 7 (Panel A and Panel B) shows the microcolumn activity testing results obtained by injecting Agilent's DB-5 microbore column test mix (contents listed in Table 2, below). Panel A, is a chromatograph of test mix injections on an Ah3P deactivated, OV-5 coated, no-postcoated microcolumn, and Panel B is a chromatograph of test mix injections on an Ah3P deactivated, OV-5 coated, PMP postcoated microcolumn. The mix was formulated to detect the presence of different characteristic active sites in the microcolumn. The mix contains n-octanol and n-decanol for the detection of hydrogen binding sites such as silanol (Si—OH) groups. 2,6-dimethylphenol and 2,6-dimethylaniline were used for Lewis acidic and basic active site detection. The metal adsorptive sites were detected using napthalene. The methyl decanoate and alkanes were used for computing microcolumn efficiency and checking presence of dead volumes and microcolumn overloading.

TABLE 2

| No. | Compound |
| --- | --- |
| 1 | Hexane |
| 2 | Decane |
| 3 | n-Octanol |
| 4 | 2,6-dimethyl phenol |
| 5 | 2,6-dimethyl aniline |
| 6 | Napthalene |
| 7 | n-Decanol |
| 8 | Tridecane |
| 9 | Methyl decanoate |

The numbers in Table 2, above, correspond to the numbered peaks in FIG. 7, Panels A and B. As shown in FIG. 7, Panel A, test mix injection on the microcolumn showed strong adsorption of n-octanol, n-decanol and 2,6-dimethylaniline peaks. The n-octanol peak was present in tailing parts of peak 4. This was confirmed using mass spectrometry. The n-decanol peak eluted as a shoulder to the baseline at 135 seconds on the chromatogram. The napthalene peak exhibit slight tailing characteristics. The number of theoretical plates were calculated based on the tridecane peak. The tridecane peak showed an adjusted retention time ($t_R$) of 1.773 minutes and a peak width of 0.034 minutes. Using equation (1) number of theoretical plates were calculated to be about 15000.

As shown in FIG. 7, Panel B, test mix injection on the PMP treated microcolumn exhibited sharp peaks for n-octanol, n-decanol and 2,6-dimethylaniline elution. N-decanol exhibited slight tailing characteristics. The tridecane peak was eluted at an adjusted retention time of 1.802 minutes and had a peak width of 0.033 minutes. The number of theoretical plates on the PMP treated microcolumn were calculated to be about 16500.

Among the post-coating treatments, resilylation reduced the phosphonate retentive nature of the microcolumn, however the tailing behavior remained. Heat treatment with PMP showed reduction in DIMP peak tailing behavior and produced a sharp peak profile. Microcolumn test mix results showed that OV-5 coated microcolumn with Ah3P deactivation showed high adsorption activity for n-octanol, n-decanol and 2,6-dimethylaniline, indicating presence of hydrogen bonding sites and acidic sites or hydrogen bonding sites of acidic nature. PMP treatment caused suppression of microcolumn activity towards octanol, decanol and dimethylaniline by poisoning the active sites. Commercial microcolumn test mix injection showed a significant decrease in the microcolumn's hydrogen bonding sites of acidic nature with PMP treatment. The theoretical number of plates on a 3 meter microcolumn increases with PMP treatment by about 1500. This corresponds to an increase of about 3% in theoretical plate numbers on one meter basis. This may be due to swelling of the stationary phase or inconsistency in the dynamic coating process.

Figure 8:
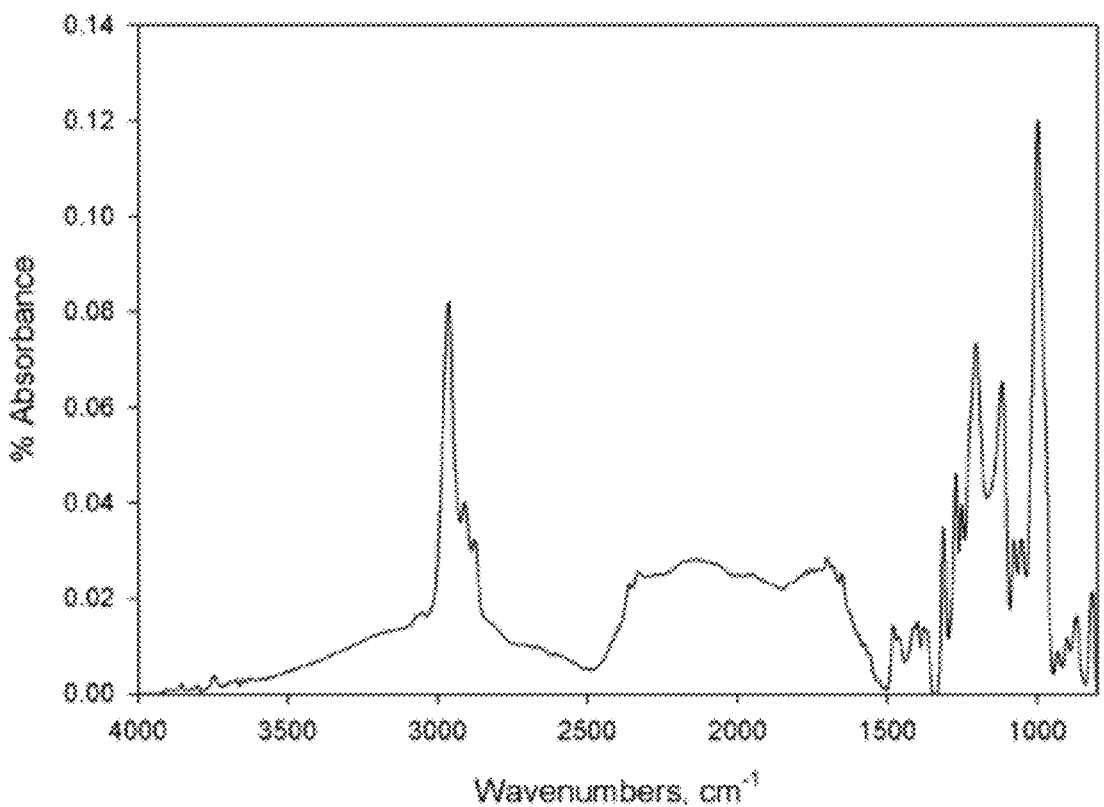
FIG. 8 is a Fourier transform infrared spectrum of a PMP treated OV-5 microcolumn constructed according to principles of the invention.

FIG. 8 is a FITR spectrum that was obtained by subtracting the FTIR results for PMP postcoated from no-postcoated OV-5 coated, Ah3P deactivated microcolumns. Strong phosphoryl stretching vibration (P═O) was evident at 1205 cm$^{-1}$. This indicated the presence of adsorbed phosphonates species on the surface. The spectrum region from 3000 cm$^{-1}$ to 2800 cm$^{-1}$ shows a typical fingerprint exhibited by $CH_3O$ and $CH_3P$ vibrations in the condensed-phase PMP spectrum. The spectrum shows presence of pinacolyl skeletal vibrations from 1240-1270 cm$^{-1}$.

Interpretation of the FITR spectra of compounds containing both P—OH and P—OR functionalities in alkyl hydrogen methylphosphonates was complicated by the fact that they give rise to strong P—O— stretching vibrations, which was common to both groups. In the spectrum, P—O—C group presence produced a strong absorption band in the region of 1000 cm$^{-1}$. Unlike the liquid PMP spectrum showing three broad peaks around 1000 cm$^{-1}$, the spectrum in FIG. 8 shows only one absorption band. That fact combined with the absence of O—H stretching absorption peak in the region of 2525-2780 cm$^{-1}$ implied that the final microcolumn comprised the species of the form in Formula 3

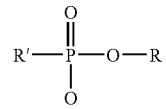

Formula 3

FTIR results indicated the presence of PMP after PMP heat treatment of coated microcolumns in vacuum. FTIR results in conjunction with GC analysis indicated that PMP chemisorbs at the active sites responsible for organophosphonate peak tailing. When the same amounts of liquid DMMP, DIMP, DEMP or TEP were injected, the subsequent organophosphonate headspace injections did produce sharp peaks. The passivation performance, however, degraded and returned to as it was, in less than about 10 minutes at oven temperature and inlet pressure of about 200° C. and about 40 psi respectively. In contrast, PMP postcoating resulted in good peak shapes for subsequent organophosphonate headspace injections and also the performance remained consistent for 8 days of testing. Structurally PMP is different from the other phosphonates due to the presence of a phospho hydroxyl (P—O—H) bond rather than the phospho ester bond (P—O—C) found in DIMP. Apart from being a heavy phosphonate, PMP may poison the active sites because the P—O—H bond reacts with the active sites and replaces the hydrogen.

Without further elaboration, it is believed that one skilled in the art using the preceding description can utilize the invention to the fullest extent. The following examples are illustrative only, and not limiting of the disclosure in any way whatsoever.

EXAMPLES

Preparatory Example 1

Microcolumn Fabrication

Microfabrication started with a double side polished four inch (5-20 ohms-cm) p type silicon wafer from SiliconQuest (Santa Clara, Calif.). The wafer was coated on both sides with Shipley SPR220-7 photoresist at 3000 rpm. Double side photolithography was performed to obtain an image of 100 microns wide and 3 meters long channel on the front side and 210 microns port holes on the back side. A hard bake at about 140° C. was performed for about 30 minutes to withstand the further deep reactive ion etching 100 microns on the channel side and through access holes in silicon on the back side.

Four 3 meter long microcolumns were obtained from processing one silicon wafer. The resulting microcolumns were cleaned with Shipley Microposit Remover 1165 at 120° C. followed by a standard clean 1 (SC-1) at 73° C. Pyrex 7740 glass pieces of the size of silicon die are cut out from wafers using diamond wheel cutter, followed by an SC-1 clean. Silicon channels were anodically sealed with the cleaned Pyrex glass at about 400° C. with 900 V bias. The bonded microcolumn was packaged in the manifold only after the deactivation step.

Preparatory Example 2

Deactivation of the Microcolumn

Three different deactivation procedures were performed; silylation, persilylation, and organosilicon hydride treatment. Silylation was performed with a 10% DMDCS ((Gelest, Boston, Mass.) solution in toluene, passed through the microcolumn heated at 100° C. for about 8 hours, followed by a toluene, methanol and ether rinse. The microcolumn was then dried under nitrogen flow prior to testing.

Persilylation and organosilicon hydride deactivation was performed using Ah3P (Gelest, Boston, Mass.) and DPT-MDS ((Fluka, Santa Clara, Calif.), respectively. The deactivation was performed by dynamically coating the surface with a one microcolumn length plug of neat reagent. A brass reservoir manifold containing the solution was attached on one of the access ports and the plug was pulled using a 26" Hg vacuum at the second access port. After the liquid plug evacuation the microcolumn was heat-treated in a vacuum annealer (300 microns Hg) at a rate of about 8° C. $\min^{-1}$ to about 375° C. and held at the final temperature for 4 hours. The vacuum annealer was purged with nitrogen for about 20 minutes before applying vacuum to ensure oxygen absence. The microcolumn was cooled to room temperature before exposing to atmosphere. The microcolumn was connected to 0.5 meter long fused silica transfer lines using a brass manifold as shown in FIG. 1C. A two ferrule design consisting of a polyimide ferrule deforming the polytetrafluoroethylene (PTFE) ferrule to achieve a leak-tight seal between the fused silica capillaries and the chip (see FIG. 1D). The packaged microcolumn was rinsed with one microcolumn volume of methanol and pentane at 25 μl/min followed by one microcolumn volume of air using a syringe pump.

Preparatory Example 3

Stationary Phase Coating

A 5% polar phase was chosen to achieve separation of phosphonates. The 4% (w/v) coating solution was prepared by dissolving OV-5 vi (Ohio Valley, USA) vi phase in pentane in a sonicator bath. Dicumyl peroxide (DCP) (Sigma Aldrich, Santa Clara, Calif.) in the form of 2% (w/v) toluene solution was added to the coating solution to achieve a final concentration of 0.2% (w/w) in the deposited stationary phase. The microcolumn was filled with the coating solution and dynamically driven out with air at a rate of 25 μl/min. The coated microcolumn was then connected to a conventional GC to perform cross-linking at about 140° C. for 1 hour with hydrogen flowing at a pressure of 5 psi. The conditioning of microcolumn was performed by heating the microcolumn to about 200° C. for 4 hours with hydrogen flow rate of 40 psi. Upon cooling the microcolumn, the fused silica connection lines were replaced with new deactivated fused silica lines. The later procedure ensured the true measurement of the microcolumn's performance. The fused silica legs were trimmed to the shortest length required for connection in a conventional GC.

Preparatory Example 4

Postcoating Treatments

Two post-microcolumn treatments were performed, one with PMP (Sigma Aldrich, Santa Clara, Calif.) and one with Rejuv-8 (Sigma Aldrich. Santa Clara, Calif.). The PMP treatment was performed on a conventional GC at 110° C. by injecting 1 microliter of liquid splitlessly with a hydrogen flow at 40 psi followed by a stabilizing time of 1 hour with the hydrogen flowing. The microcolumn was reconditioned at 200° C. with 40 psi inlet pressure for 4 hours. The reconditioning end was checked with the presence of a stable FID baseline.

The resilylation treatment with Rejuv-8® was performed by four injections each one hour apart. Each injection consisted of 5 microliters of liquid at 100° C. with inlet pressure of 10 psi. The resilylation treatment was followed by reconditioning treatment stated earlier.

Specific Example 5

Microcolumn Testing

An Agilent 6893N GC/FID-MS, with 7683B autosampler was used for all the separations. Packaged microcolumn was placed in the GC and connected to the split inlet and FID using a Restek deactivated guard microcolumns. Hydrogen was used as carrier gas in all tests except when carrying out Agilent microcolumn testmix injection. Helium was used in the later case. Headspace injections of DIMP (Alfa Aesar, Ward Hill, Mass.) and n-octanol (Sigma Aldrich, Santa Clara, Calif.) were performed to quick-check microcolumn activity. DIMP was used a representative phosphonate tracer. Octanol was selected because it is a very sensitive probe for microcolumn deactivation problems. The deactivation optimization tests were performed on 35 cm long microcolumns injecting 5 μl headspace with a split of 50:1 and oven temperature and inlet pressure held at 75° C. and 5 psi respectively.

The effect of post-coating treatment on phosphonate activity was carried out on 3 meter long, OV-5 coated, Ah3P deactivated microcolumns by injecting 5 μl DIMP headspace with a split of 50:1 and microcolumn temperature and pressure at 110° C. and 20 psi, respectively. Detailed study of microcolumn activity was performed using DB-5 microbore microcolumn test mix supplied by Agilent (Santa Clara, Calif.). The 1 μl of test mix liquid was injected with a split of 1000:1. The inlet pressure adjusted to achieve a helium carrier gas velocity of 20 cm/s. The oven temperature was adjusted to 120° C. to achieve a retention factor of about 6 for tridecane.

The chromatograms were analyzed using Agilent's MSD-Chem data analysis software. Microcolumn plates were calculated using the tridecane peak in the Agilent microcolumn test mix injection as follows:

$$N = 5.54 \cdot \left(\frac{t'_R}{W_h}\right)^2 \quad (1)$$

where, $t_R'$ is retention time of the tridecane minus methane retention time. $W_h$ is width of the tridecane peak, taken at ½ the peak height.

Specific Example 6

Infrared Analysis

Fourier transform infrared spectroscopy (FTIR) was performed on silicon samples to further understand the effect of the PMP treatment. A double side polished four inch silicon wafer was spin coated with neat Ah3P solution at 3000 rpm for 40 seconds. The coated wafer was then heated in a vacuum annealer as previously described for the microcolumn deactivation. OV-5 coating solution was prepared as mentioned earlier for microcolumn coating procedure in Preparatory Example 3, supra. Deactivated wafer pieces were spin coated with the coating solution at 3000 rpm followed by a cross-linking treatment in a vacuum annealer at 140° C. for 1 hour. PMP treatment of the coated silicon piece was performed by spin coating neat PMP solution at 3000 rpm followed by heat treatment at 200° C. in the vacuum annealer. PMP vaporization was found to be complete in a control experiment under these treatment conditions. The treated surfaces were analyzed using a Nicolet Nexus 670 FTIR in the transmission mode. IR Spectra was collected in the transmission mode with 64 scans from 800 to 4000 $cm^{-1}$ with a resolution of 2 $cm^{-1}$. ACD/SpecManager software was used to perform suitable background correction to the IR spectrum.

Specific Example 7

Dynamic Coating of Stationary Phase for Microcolumn Preparation

Model Capillary Preparation

A 15 m long spool of square capillary (100 μm×100 μm I.D., 365 μm O.D., Polymicro Technologies) was passivated using a dynamic vapor-phase silylation method known in the art. Rejuv® (Sigma Aldrich, a commercial silylating mixture of n,O-bis(trimethylsilyl)acetamide, hexamethyldisilazane, and 1-(trimethylsilyl)imidazole) was used as the silylating reagent. Following the passivation the square capillary was cut into 1 m long sections for dynamic coating according to the design of experiments.

Coating Solution Preparation

5% polar stationary phase, OV-5 vinyl gum obtained from Ohio Valley Specialty Company (Marietta, Ohio) was chosen as the stationary phase due to its wide applicability. The coating solutions were prepared in hexamethyldisilazane treated 12×32 vials obtained from Alltech (#72670). The required amount of stationary phase was transferred to a vial and adequate quantity of 0.2 μm filtered pentane was injected into the capped vial using a syringe to produce the required concentration of coating solution. The stationary phase was dissolved by sonicating the vial for 20 minutes. Dicumyl peroxide (DCP) (Sigma Aldrich, >99%) in the form of freshly prepared 2% (w/v) pentane solution was added to the coating solution to achieve a DCP concentration of 1% (w/w of the stationary phase).

Mode-Column Coating Process

Figure 9:
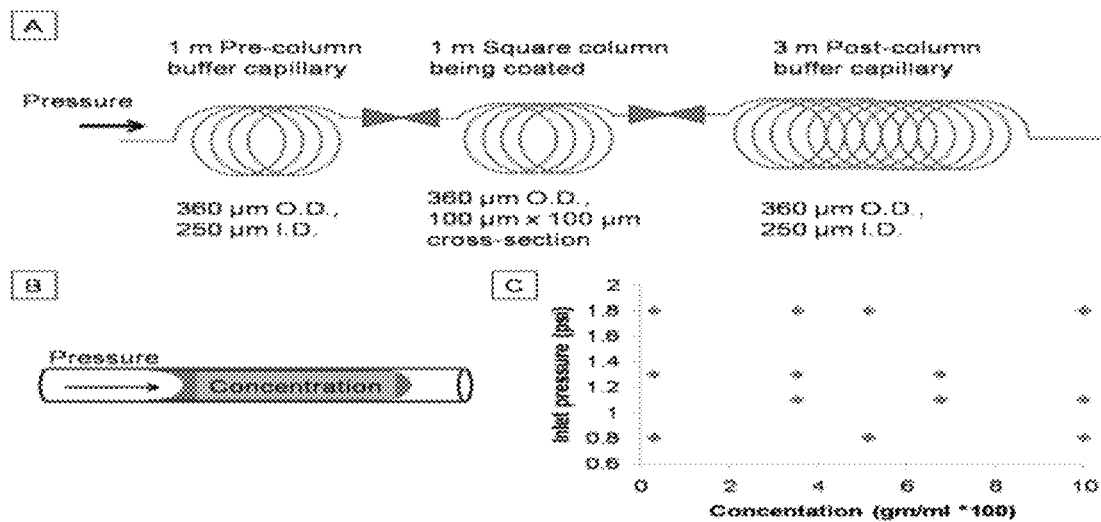
FIG. 9 is a schematic showing the column arrangement during the dynamic coating of a 1 m long square capillary column (Panel A), variables altered in coating the column (Panel B), and the design of experiment implemented.

The column coating process was performed inside a conventional GC oven. As shown in FIG. 9, Panel A, 1 m and 3 m long capillaries (250 um I.D., 360 um O.D.) were used as pre-column and post-column buffer respectively, for flow restriction. The square capillaries were connected to the buffer capillaries using Teflon® tubing sleeve (Upchurch Scientific, F-243X) and a Swagelok 1/16" union. The coating process proceeded by filling the coating solution in the square capillary plus the post-column buffer and then connecting the square capillary to the GC inlet via the pre-column buffer. The square column and the post-column buffer were immersed in a 22° C. water bath during the coating process. The GC inlet system was used to apply the coating pressure (split flow of 100:1 provided good stability and accuracy). After the coating solution exited the post-column buffer was disconnected and the carrier gas inlet pressure was pulsed to 20 psi for a short duration. This step allowed drying all the solvent post deposition. The GC inlet pressure was then set to 0.8 psi and the deposited stationary phase was cured by rapidly heating the GC oven and holding at 110° C. for 10 minutes, followed by overnight treatment at 140° C. for complete curing. The next day columns were conditioned at 200° C. for 1 hour, cooled down to room temperature and trimmed to 0.8 m length for chromatographic evaluation.

Coated Column Tests

An Agilent 6893N GC/FID-MS equipped with 7683B auto-sampler was used for all the separations. The chromatograms were recorded using the MSD Chemstation software and processed using the Peakfit software (v4.12). Helium was used as the carrier gas in this paper. The injector temperature was held at 250° C. Methane injections were used to measure the average velocities. Isothermal test mixture was prepared using puriss-grade chemicals (GC standards) from Aldrich (Milwaukee, Wis.).

Isothermal chromatographic performances of the square columns were tested by isothermally separating $C_{10}$ to $C_{12}$ n-alkanes on the columns held at 70° C. A standard containing the alkanes (1000 ppm each) was prepared in an n-$C_5$ matrix and 1 μl of the standard was injected with a split of 1000:1 into the coated square capillary columns. The carrier gas velocity was maintained at 25 cm/s in all isothermal separation tests.

Temperature-programmed separation performances of the coated square columns were obtained by injecting 1 μl of a Grob's mix (Alltech, 41761) with a split of 1000:1. The coated square columns were held at 30° C. and ramped to 150° C. at the rate of 2.96° C./min. The carrier gas velocity was held constant at 28 cm/s in all temperature programmed separation tests.

Design of Experiment (DoE), Analysis, and Optimization

FIG. 9, Panel B, shows the diagram of dynamic coating and the coating variables that were varied in this example. FIG. 9, Panel C shows the adapted E-Chip software generated D-optimal design to test the different combinations of dynamic coating parameters viz. coating solution concentration and square root of the coating pressure, each as a continuous variable in the range of 0.3-10 (w/v) % and 0.8-1.8 psi, respectively. The ranges were restricted by the feasibility of conducting coating experiments. Outcomes of the coating process were measured in two chromatographic separation modes: retention times ($t_R$) and theoretical plate numbers (N) for $C_{11}$ and $C_{12}$ n-alkane peaks and resolution ($R_S$) for the latter peak pair were measured in the isothermal separation mode; elution temperatures (T) for methyl decanoate (E10) and methyl dodecanoate (E12) peaks and Trennzahl number (TZ) for the latter peak pair were measured in the temperature programmed separation mode. Theoretical plate number (N), Resolution ($R_S$) and Trennzahl numbers (TZ) were calculated by, $$N = 5.54 \cdot \left(\frac{t_R}{w_h}\right)^2 \quad (2)$$

$$R_S = \frac{2 \cdot (t_{R2} - t_{R1})}{w_{h1} + w_{h2}} \quad (3)$$

$$TZ = \frac{t_{R2} - t_{R1}}{w_{h1} + w_{h2}} - 1 \quad (4)$$

where, $t_{R1}$ and $t_{R2}$ are the retention times, and $w_{h1}$ and $w_{h2}$ are the peak widths at half height of peaks 1 and 2 respectively. The experimental data was fit to a quadratic model, $$R = A_0 + A_1 \cdot c + A_2 \cdot p + A_3 \cdot c \cdot p + A_4 \cdot c^2 + A_5 \cdot p^5 \quad (5)$$

where, R is the response variable, $A_0$-$A_5$ are model coefficients, c is the coating solution concentration, and p is the coating pressure.

Optimization of coating parameters was carried out by: simultaneous maximization of theoretical number of plates and resolution for isothermal separations, and maximization of Trennzahl number for temperature programmed separation.

Translation of DoE Results to Coat Micro-Columns

The dynamic coating parameters to obtain efficient columns were identified by optimization of isothermal and temperature-programmed elution characteristics (resolution, Trennzahl number, and theoretical plate numbers). The suitable concentration found could be directly utilized in coating micro-columns; however the coating pressure had to be translated to methane retention times that reflected the permeability of the micro-columns to be coated.

Design and Fabrication of Micro-Columns

Microfabrication started with a double side polished silicon wafer (4" diameter, 250 μm thick, 5-20 ohms-cm p-type) from Silicon Quest International. The wafer was sputter coated with 1000 Å thick aluminum on one side. The aluminum layer protected the silicon surface from getting damaged during the fabrication steps prior to anodic bonding. Shipley SPR220-7 photoresist was spin-coated on both sides of the wafer at 3000 rpm. Double side lithography was performed to obtain an image of micro-channels on the aluminum side and fluid transfer holes on the silicon side. The chrome mask set for lithography was fabricated by Photo Sciences Inc. using a laser pattern generator. Micro-channel mask consisted of four 3.2 cm×3.2 cm dies each filled with 100 μm wide and 3 m long micro-channel folded in a serpentine configuration. The second mask consisted of 210 μm wide fluid transfer holes for connecting the micro-channels from the bottom side. 10 micron wide crosses were designed in the masks to aid the alignment process. Exposed photoresist was developed in MIF327 developer. Overdevelopment with MIF327 was allowed to etch the underlying aluminum layer exposing the silicon surface for reactive ion etching. The patterned photoresist was baked at 140° C. for 30 minutes to withstand the plasma exposure in the reactive ion etching steps. Deep reactive ion etching was used to etch the channel patterns 100 μm deep and the access holes through the wafer. The wafer was diced during the latter step. The micro-column dies were cleaned with Shipley Microposit Remover 1165 at 120° C. followed by an aluminum etching in type A aluminum etchant (Transene company), and a standard clean 1 (SC-1) at 73° C. Pyrex® 7740 glass pieces approximately of the size of micro-column die were cut out from wafers using an IR laser and cleaned using an SC-1 clean procedure. Silicon micro-columns were anodically sealed with the cleaned Pyrex® glass at 400° C. with 900 V bias.

Micro-Columns Passivation

Organosilicon hydride passivation using phenyltris(dimethylsiloxy)silane (Ah3P) (Gelest, SIP6826) was performed. The passivation was performed by dynamically coating the surface with one column length plug of neat reagent. A brass reservoir manifold containing the solution was attached on one of the micro-column access ports and the plug was pulled using a 660.4 mm Hg vacuum at the second access port. After the liquid plug exited the micro-column was heat-treated in a vacuum annealer (300 microns Hg) at a rate of 8° C. min$^{-1}$ to 375° C. and holding at the final temperature for 4 hours. The vacuum annealer was purged with nitrogen for 20 minutes before applying vacuum to ensure oxygen absence. The micro-column was cooled to room temperature before exposing to atmosphere.

Micro-Column Coating Process

The ends of the micro-column were connected to a 1 m and 3 m long fused silica capillary (100 μm I.D. and 200 μm O.D., Polymicro technologies, TSP100200) using Nanoports® (Upchurch Scientific, N-125S). Special fluorosilicone gaskets were used with Nanoports® to create a low dead volume connection. The coating solution from a gas tight syringe was pushed using mild hand pressure to fill the micro-column and buffer capillaries. The syringe was disconnected when four drops of coating solution left through post-column buffer capillary end. The pre-column buffer was attached to a GC inlet and the coating solution was driven out using calculated pressure corresponding to the required methane retention times. When the coating solution exited the post-column buffer capillary, the solvent from the coated stationary phase was removed by pulsing the inlet pressure to 20 psi for a short duration. Subsequently, the inlet pressure was reduced to 0.8 psi and the stationary phase was cross-linked and conditioned by heating the micro-column to 140° C. overnight.

Post-coating pinacolyl methylphosphonic acid (PMP) deactivation treatments was performed. The PMP treatment was performed on a conventional GC at 110° C. by injecting 1 μl of liquid PMP in the splitless mode (injector temperature of 250° C.) with a helium flow at 20 psi followed by a stabilizing time of 1 hour with the carrier gas flowing. The micro-column was reconditioned at 200° C. with 20 psi inlet pressure for 4 hours. The completion of reconditioning process was checked with the presence of a stable FID baseline. The connecting fused silica capillaries were replaced with Restek deactivated guard capillaries (100 μm I.D., 200 μm O.D., and 25 cm long, IP deactivated) and the latter was trimmed to the required minimum length prior to testing.

Design of Experiment Analysis

Chromatography was performed to compare the isothermal separation of alkanes and temperature programmed separation of Grob's mix obtained by changing the coating plug concentration or the coating pressure. Increasing the coating pressure from 1.1 psi to 1.8 psi while holding the coating solution concentration constant at 3.5 (w/v) % produced square columns with higher retention times in isothermal and temperature programmed separation. The isothermal retention times of $C_{10}$, $C_{11}$, and $C_{12}$ increased from 6.5, 9.8, and 13.3 seconds respectively to 6.8, 10.2, and 13.7 seconds respectively. The temperature programmed retention times of E10, E11, and E12 increased from 6.45, 9.76, and 13.27 minutes respectively to 6.81, 10.18, and 13.73 minutes respectively. Similarly increasing the coating solution concentration from 3.5 (w/v) % to 6.76 (w/v) % while holding the coating pressure constant at 1.1 psi also produced square column with higher retention times in isothermal and temperature programmed separation. The isothermal retention times of $C_{10}$, $C_{11}$, and $C_{12}$ increased from 6.5, 9.8, and 13.3 seconds respectively to 8.3, 11.8, and 15.4 seconds respectively. The temperature programmed retention times of E10, E11, and E12 increased from 6.45, 9.76, and 13.27 minutes respectively to 8.27, 11.76, and 15.38 minutes respectively.

The separation parameters: retention times ($t_R$), effective theoretical plate numbers (N) and resolution ($R_S$) for C11 and C12 peaks for isothermal separations; elution temperatures (T), and Trennzahl numbers (TZ) for temperature-programmed separations, were modeled with a quadratic equation. Model surface plots were generated which predicted the isothermal retention times of $C_{11}$ (A) and $C_{12}$ (B) on square capillaries coated with various coating pressures and coating solution concentrations. The quadratic model was found to predict the $C_{11}$ and $C_{12}$ isothermal retention times with an R-squared value of 0.92. The fitting routine predicts that concentration, concentration-squared and pressure-squared terms play the most important role in determining the retention times. Increasing the coating concentration was found to increase the isothermal retention times regardless of the coating pressure; however increasing the coating pressure led to a point of minimum retention at all concentrations. Increasing the coating pressure past this value of minimum retention was found to increase the retention times. The coating pressure corresponding to the minimum retention point was found to be about 1.5 psi in the low coating concentration range (0.3 to 2 (w/v) %) and was found to shift to 1.3 psi in the high coating concentration range (7-10 (w/v) %).

A plot of the model surface and experimental data for the effective number of theoretical plates (N) was calculated based on the isothermal $C_{11}$ and $C_{12}$ elution as a function of the dynamic-coating pressure and concentration used to coat the square capillaries. The quadratic model was found to predict N for $C_{11}$ and $C_{12}$ isothermal elution with an R-squared value of 0.92 and 0.95 respectively. The fitting routine predicts that concentration and concentration squared terms play the most important role in determining the theoretical plate numbers. The model predicts that the value of N for square capillaries coated with less concentrated solutions increased from 16 to 180 plates/m with the increase in coating pressure from 0.8 to 1.8 psi; however the effect of coating pressure on N was found to be negligible as the coating concentration increased above 3 (w/v) %. N was found to increase with the increase in coating solution concentrations and to plateau at N values of 3500-4000 plates/m with higher coating concentrations irrespective of the coating pressure.

A plot of model surface and experimental data for the resolution between the isothermally eluted $C_{11}$ and $C_{12}$ peaks as a function of dynamic coating pressure and concentration used to coat the square columns was generated. The quadratic model was found to predict the resolution between the $C_{11}$ and $C_{12}$ peaks with an R-squared value of 0.97. The fitting routine predicts that concentration, concentration multiplied by pressure, and concentration squared terms play the most important role in determining the resolution. The resolution was found to be independent of the dynamic coating pressure except at low coating solution concentrations. The resolution was found to increase with the increase in coating solution concentration and then plateau to a value between 16.5 and 18.5 above 6 (w/v) % concentrations.

A plot of the model surface and experimental data for elution temperatures corresponding to the E10 and E12 as a function of dynamic coating pressures and concentrations was generated. The quadratic model was found to predict the elution temperatures for $E_{11}$ and $E_{12}$ during the temperature programmed separations with an R-squared value of 0.9. The elution temperatures were found to increase as the coating concentration was increased. The elution temperatures were found to increase on increasing the coating pressures at low concentrations; however at higher coating concentrations, the elution temperatures were not found to depend on the coating pressure.

The model surface plot and experimental data for the Trennzahl numbers (TZ) corresponding to the E10 and E12 fatty acid methyl ester elution on square columns coated with different coating pressures and concentrations was generated. The quadratic model was found to predict the Trennzahl numbers for E11 and E12 temperature programmed elution with an R-squared value of 0.66. The model does not adequately predict the TZ value but predicts only the trend in the experimental data. Regardless of the coating pressure, the change in coating concentration from 3.5 to 10 w/v % changes the TZ value changes from about 13 to about 20. Changing the pressure had minor effect on the TZ values particularly at low concentrations; however at higher concentrations, the TZ values were found to decrease with increasing coating pressures.

Figure 10:
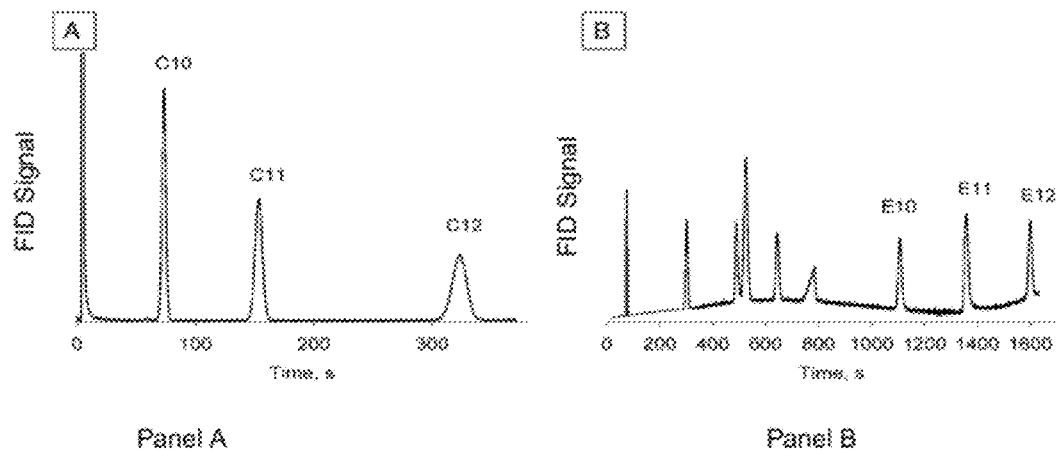
FIG. 10 shows two chromatograms showing separation of n-$C_{10}$ to n-$C_{11}$ alkanes (Panel A) and Grob's mix (Panel B) on square capillary column coated with parameters (0.9 psi pressure and 10 w/v % concentration) that would allow creating square column with best performance as indicated by the model optimization.

The optimization was carried out by simultaneously maximizing theoretical number of plates for $C_{11}$ and $C_{12}$ peaks, the resolution between the latter peaks, and the Trennzahl number for E11 and E12 peak pair. The optimization routine predicted that the optimum point lies at a coating concentration of 10 w/v % and coating pressure of 0.9 psi. Due to the insufficient fit of the model to the Trennzahl numbers, exclusion of the latter was also tried in the optimization process; however there was no difference in the optimum point values. The quadratic model predicted an $R_S$ value of 18.46 within 95% confidence intervals of 20.51 and 16.39. The predicted $N_{C11}$ and $N_{C12}$ values were 4165 and 3854 within the 95% confidence intervals of (2754, 5866) and (2832, 5032). FIG. 10 shows the isothermal (A) and temperature-programmed (B) separation chromatograms obtained on a square capillary coated with the optimized dynamic coating parameters. The experimental values of theoretical plate numbers for the $C_{11}$ and $C_{12}$ peaks and the resolution between the pair of latter peaks were found to be 2664, 3003, and 16.95.

Translation of DoE Results to Coat Micro-Columns

Figure 11:
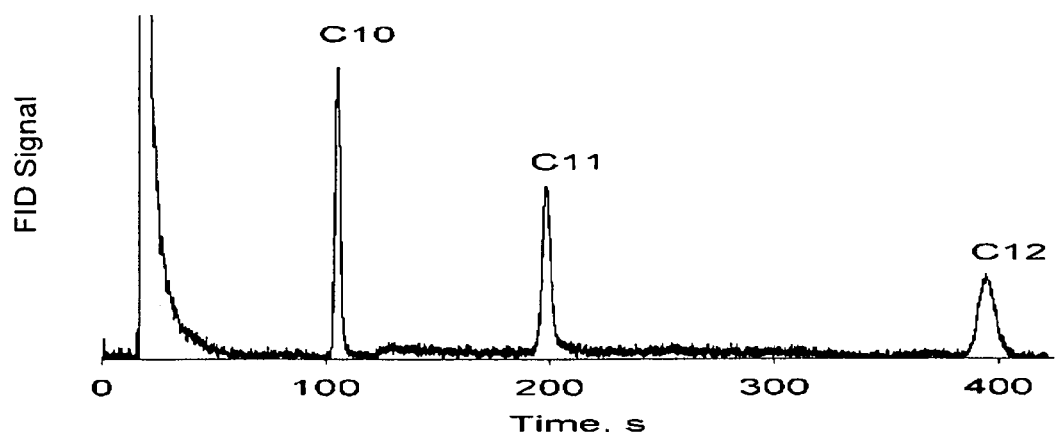
FIG. 11 shows two chromatograms showing separation of n-$C_{10}$ to n-$C_{11}$ alkanes (Panel A) and Grob's mix (Panel B) on square capillary column coated with parameters (2.7 psi pressure and 10 w/v % concentration) that would allow creating square column with better performances as indicated by the model optimization.
Figure 11:
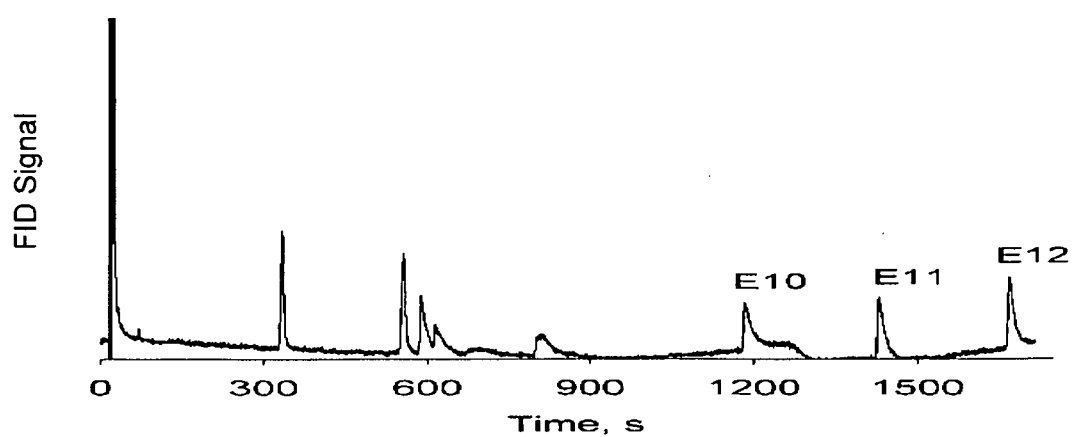

Average velocity of 1.03 cm/s was found on the square capillary setup including the buffer columns at an inlet pressure of 0.9 psi. Translation of DoE findings to micro-column coating was achieved by using the coating pressure that was required to obtain a velocity of 1.03 cm/s on the micro-column setup. FIG. 11 shows the $C_{10}$-$C_{12}$ n-alkane separation chromatogram on a micro-column coated with optimized conditions. The experimental values of theoretical plate numbers for the $C_{11}$ and $C_{12}$ peaks and the resolution between the pair of latter peaks were found to be 8311, 10742, and 29.46. Temperature programmed separation on coated micro-columns yielded a TZ of 19 between E10 and E12.

This example characterized the dynamic coating of stationary phase in the square DRIE microfabricated columns using model square fused silica capillaries. Optimization of the model square column coating parameters to obtain high N, $R_S$, and TZ values suggests that dynamic coating should be performed with high coating solution concentrations and lower coating pressures.

Experiments with higher concentrations required high pressures to fill the 100 μm×100 μm I.D, 1 m long square column plus the 3 m long post-column buffer during the coating process. This example showed that a maximum concentration of 10 (w/v) % for the OV-5 vi gum could be safely used with leakage. A minimum coating pressure of 0.8 psi accurately using a conventional-GC inlet was applied. The optimization routine resulted in an optimum coating pressure and concentration of 0.9 psi and 10 w/v % respectively. The model square column coated with the optimized dynamic coating parameters produced theoretical number of plates for $C_{11}$ and the resolution between $C_{11}$ and $C_{12}$ peaks during the isothermal separation within the 95% confidence interval of that predicted by the quadratic model. However the number of theoretical plates for $C_{12}$ peak was below that predicted by the model. This could have occurred due to the error in preparing accurate coating solution concentrations. The design of experiments carried out on square fused silica capillaries was found to be successfully transferred to making high performance micro-columns.

The general trend in the separation results from columns coated with different coating pressures and concentrations was found to be congruent with the theoretical predictions. The retention times of alkanes ($C_{11}$ and $C_{12}$) in isothermal separations and fatty acid methyl esters (E10 and E12) in temperature programmed separations increased with the increase in coating solution concentration. This confirms the increase in stationary phase film thickness on increasing the coating solution concentration. The retention times in temperature programmed separations are also found to constantly increase as a function of the coating pressure and are in agreement to what the theoretical coating equations predict. However the isothermal n-alkane retention times were not found to be an increasing function of coating pressure in the tested range. The model surface for isothermal retention times predicts that there exists a minimum retention time point as the coating pressure is varied.

The examples given above are merely illustrative and are not meant to be an exhaustive list of all possible embodiments, applications or modifications of the invention. Thus, various modifications and variations of the described methods and systems of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention which are obvious to those skilled chemical and/or mechanical engineering or in the relevant fields are intended to be within the scope of the appended claims.

The disclosures of all references and publications cited above are expressly incorporated by reference in their entireties to the same extent as if each were incorporated by reference individually.

What is claimed is:

1. A Gas chromatography (GC) column, comprising:
   a plurality of column walls each having a deactivated inner surface;
   a stationary phase layer deposited on the deactivated inner surface of said plurality of column walls;
   a plurality of binding sites in said stationary phase layer; and
   a post-coating molecule bound to at least one of said plurality of binding sites in said stationary phase layer;
   wherein the post-coating molecule is one or more compounds selected from the group consisting of a thiol, a phosphine, an amine,

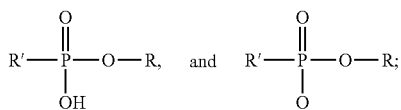

wherein R and R' are linear, branched, or substituted hydrocarbons.

2. The GC column of claim 1, wherein the inner surface of said plurality of column walls has been deactivated with a compound selected from the group consisting of DMDCS, Ah3P, and DPTMDS.

3. The GC column of claim 1, wherein said stationary phase layer has a thickness of about 0.1 μM.

4. The GC column of claim 1, wherein said stationary phase layer is uniformly spread over the inner surface of said plurality of column walls.

5. The GC column of claim 1, wherein said plurality of column walls has a serpentine configuration.

6. The GC column of claim 1, wherein said plurality of column walls are rounded.

7. The GC column of claim 1, wherein said post-coating molecule comprises a structure of Formula I:

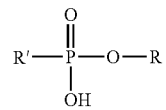

Formula 1 where R and R' are linear, branched, or substituted hydrocarbons.

8. The GC column of claim 1, wherein the post-coating molecule comprises the structure of Formula II:

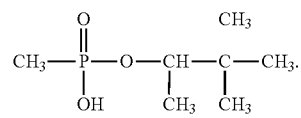

Formula 2

9. A method for preparing a gas chromatograph (GC) column, said method comprising the steps of
   deactivating a plurality of walls of a GC column;
   depositing a stationary phase in the GC column; and
   treating the GC column with a molecule such that the molecule binds to active sites in the stationary phase of the column;
   wherein the molecule is one or more compounds selected from the group consisting of an acid including hydrocarbon ligands, a base including hydrocarbon ligands, a thiol, a phosphine, and an amine.

10. The method of claim 9, wherein the stationary phase in said depositing step is applied at a pressure of about 0.9 psi and at a concentration of about 10 w/v %.

11. The method of claim 9, wherein the deactivating step comprises a method selected from the group consisting of silylation, perisilylation, and deactivation using an organosilicon hydride.

12. The method of claim 11, wherein the silylation is performed using DMDCS, the perisilylation is performed using Ah3P, and the deactivation with the organosilicon hydride is performed using DPTMDS.

13. The method of claim 9, wherein the molecule in said treating step comprises a structure of Formula I:

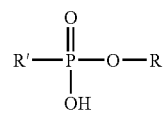

Formula 1 where R and R' are linear, branched, or substituted hydrocarbons.

14. The method of claim 13, wherein the molecule comprises the structure of Formula II:

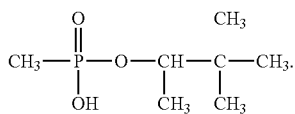

Formula 2

15. A gas chromatograph (GC) column prepared by the method of claim 9.

16. The GC column of claim 15, wherein the molecule in said treating step comprises a structure of Formula I:

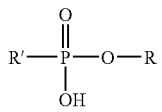

Formula 1 where R and R' are linear, branched, or substituted hydrocarbons.

17. The GC column of claim 15, wherein the molecule comprises the structure of Formula II:

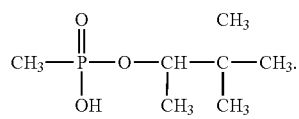

Formula 2

18. The GC column of claim 15, wherein the molecule comprises the structure of Formula III:

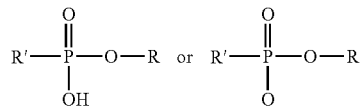

where R and R' are linear, branched, or substituted hydrocarbons.

* * * * *